(12) United States Patent
Yin et al.

(10) Patent No.: US 10,054,735 B2
(45) Date of Patent: Aug. 21, 2018

(54) METHOD AND APPARATUS FOR PRODUCING CRYSTALLINE CLADDING AND CRYSTALLINE CORE OPTICAL FIBERS

(71) Applicants: The Penn State Research Foundation, University Park, PA (US); General Opto Solutions, LLC, State College, PA (US)

(72) Inventors: Shizhuo Yin, State College, PA (US); Fang Luo, State College, PA (US)

(73) Assignees: The Penn State Research Foundation, University Park, PA (US); General Opto Solutions, LLC, State College, PA (US)

( * ) Notice: Subject to any disclaimer, the term of this patent is extended or adjusted under 35 U.S.C. 154(b) by 0 days.

(21) Appl. No.: 15/791,762

(22) Filed: Oct. 24, 2017

(65) Prior Publication Data
US 2018/0045883 A1    Feb. 15, 2018

Related U.S. Application Data

(63) Continuation-in-part of application No. 15/220,807, filed on Jul. 27, 2016.

(60) Provisional application No. 62/412,463, filed on Oct. 25, 2016, provisional application No. 62/282,636, filed on Aug. 6, 2015, provisional application No. 62/282,235, filed on Jul. 28, 2015.

(51) Int. Cl.
*G02B 6/02* (2006.01)
*C01F 17/00* (2006.01)
*G01N 21/64* (2006.01)
*C01G 15/00* (2006.01)
*C01G 28/00* (2006.01)
*F21V 8/00* (2006.01)
*C01F 7/00* (2006.01)

(52) U.S. Cl.
CPC .......... *G02B 6/02352* (2013.01); *C01F 7/002* (2013.01); *C01F 17/0012* (2013.01); *C01G 15/006* (2013.01); *C01G 28/002* (2013.01); *G01N 21/64* (2013.01); *G02B 6/0003* (2013.01); *G02B 6/0219* (2013.01)

(58) Field of Classification Search
CPC .............................. G01N 21/64; G02B 6/2746
See application file for complete search history.

(56) References Cited

U.S. PATENT DOCUMENTS

| 8,233,754 B2 | 7/2012 | Bohnert et al. | |
| 2005/0141836 A1 | 6/2005 | Peret | |
| 2005/0201715 A1* | 9/2005 | Ellwood, Jr. | G02B 6/2746 385/147 |

(Continued)

*Primary Examiner* — Sung Park
*Assistant Examiner* — Hoang Tran
(74) *Attorney, Agent, or Firm* — Buchanan Ingersoll & Rooney PC

(57) ABSTRACT

We provide methods and apparatus for preparing crystalline-clad and crystalline core optical fibers with minimal or no breakage by minimizing the influence of thermal stress during a liquid phase epitaxy (LPE) process as well as the fiber with precisely controlled number of modes propagated in the crystalline cladding and crystalline core fiber via precisely controlling the diameter of crystalline fiber core with under-saturated LPE flux. The resulting crystalline cladding and crystalline core optical fibers are also reported.

5 Claims, 34 Drawing Sheets

(56) References Cited

U.S. PATENT DOCUMENTS

2012/0294577 A1 11/2012 Bennett
2014/0055844 A1 2/2014 Cormier et al.

* cited by examiner

METHOD AND APPARATUS FOR PRODUCING CRYSTALLINE CLADDING AND CRYSTALLINE CORE OPTICAL FIBERS

CROSS-REFERENCE TO RELATED APPLICATIONS

This application is a continuation-in-part of and claims priority to U.S. patent application Ser. No. 15/220,807, filed on Jul. 27, 2016, which claims the benefit of priority of U.S. Provisional Patent Application No. 62/282,235, filed on Jul. 28, 2015. This application also claims the benefit of priority of U.S. Provisional Patent Application No. 62/282,636, filed on Aug. 6, 2015 and of U.S. Provisional Patent Application No. 62/412,463, filed on Oct. 25, 2016. All four of those applications are incorporated by reference herein.

FIELD OF INVENTION

Embodiments relate to methods and apparatus for fabricating crystalline cladding and crystalline core optical fibers. Applications of the clad crystalline fibers to fiber lasers, fiber amplifiers, fiber sensors, and other fiber optic components and devices are also reported.

BACKGROUND OF THE RELATED ART

The importance of crystalline optical fibers goes back at least to the introduction of laser melting technology in 1976. See, e.g., U.S. Pat. No. 3,944,640. Crystalline fibers may be, for example Neodymium (Nd)/Ytterbium (Yb)/Erbium (Er) doped yttrium aluminum garnet (YAG) fibers. In comparison to glass optical fibers, crystalline fibers offer a number of advantages. J. A. Harrington, "Single-crystal fiber optics: a review," SPIE 8959, p. 895902-1, 2014. For example, crystalline fibers typically have an absorption cross section that is an order of magnitude higher than that of a corresponding glass fiber. This not only reduces the required fiber length for lasing but also significantly mitigates the nonlinear issues.

Crystalline fibers also tend to have a much higher thermal conductivity than glass fiber. For example, a crystalline YAG fiber may have a thermal conductivity of about 10 W/m·K, compared to 1.38 W/m·K for silica fiber. This enables better thermal dissipation by the crystalline fiber. Crystalline fibers (particularly Nd/Yb/Er doped YAG fibers) have a much lower nonlinear stimulated Brillouin scattering (SBS) coefficient than that of silica fiber. This substantially reduces detrimental SBS effect and enables a higher power/energy fiber laser. The ultimate scaling potential for an Yb-doped YAG fiber has been estimated to be as high as 16.9 kW, which is about one order of magnitude higher than that of silica-based fiber laser (~1.89 kW). J. Dawson, "Power scaling analysis of fiber lasers and amplifiers based on non-silica materials," SPIE 7686, p. 768611, 2010. Finally, in addition to the potential of enabling higher power/energy fiber lasers and fiber amplifier, crystalline fibers can play an important role in harsh environment high sensitivity and selectivity fiber optic sensors. For example, since the melting temperature of crystalline sapphire fiber is higher than 2000° C., very high temperature (up to 2000° C.) fiber optic temperature sensors may be prepared. S. Yin, P. Ruffin, and F. Yu, *Fiber Optic Sensors*, CRC Press, New York, 2008. Magneto-optic crystalline fibers [e.g., bismuth substituted yttrium iron garnet (Bi:YIG) crystalline fiber] can also enable high sensitivity fiber optic magneto-optic sensors and all-fiber isolators.

Although crystalline fibers offer a great potential for high power/energy fiber lasers as well as harsh environment fiber optic sensors, the performance of current crystalline fiber optic sensors is largely compromised by a lack of a proper crystalline cladding. A proper cladding can not only reduce the scattering loss but also control the number of modes propagated in the fiber. For many applications, such as high beam quality fiber lasers, fewer or single mode operations are preferred. Unfortunately, unlike glass fiber, crystalline fibers are not pulled from a vitreous melt and therefore cladding cannot be readily fabricated in the same way as amorphous glass fibers. In the past several decades, there have been continuous efforts in developing proper cladding on crystalline fiber cores. Although there has been some progress in this field, high quality crystalline cladding and crystalline core optical fibers are still underdeveloped.

BRIEF SUMMARY OF THE INVENTION

We provide liquid phase epitaxy (LPE) methods for preparation of high quality crystalline cladding and crystalline core optical fiber. One embodiment includes the steps of reducing the diameter of crystalline fiber core preform by applying an under-saturated LPE flux, then growing a crystalline cladding layer on the core by introduction of a super-saturated LPE flux. The refractive index of grown cladding layer in a super-saturated LPE flux is different from the thinned crystalline fiber core preform (e.g., lower than the refractive index of the thinned crystalline fiber core) because the material composition of super-saturated LPE flux is different from the composition of under-saturated LPE flux. In this way, the number of modes propagated in the crystalline cladding and crystalline core fiber can be precisely controlled, which enables single or fewer mode crystalline cladding and crystalline core optical fiber.

Further embodiments provide a method of preventing thermal stresses from damaging the fiber during an LPE growing process. These embodiments may include but are not limited to use of pre-bent holding, one-end firm holding, and other holding methods. Further embodiments provide methods for producing crystalline cladding and crystalline core optical fiber by a unique hot isostatic pressing (HIP) method, wherein at least a portion of polycrystalline cladding is transformed into a single crystalline cladding through solid state conversion.

Disclosed herein is a method for forming a crystalline cladding-crystalline core fiber optical system comprising the steps of contacting a molten liquid phase epitaxy (LPE) solution with a crystalline fiber core to grow a crystalline cladding layer thereon, wherein the refractive index of the crystalline cladding layer is lower than the refractive index of the crystalline fiber core.

In one embodiment of the method, the crystalline fiber core is grown by a method selected from the group consisting of laser heated pedestal growth (LHPG) method, micropulling, and edge-defined film-fed growth (EFG) method.

In one embodiment of the method, the step of contacting the LPE solution with a crystalline fiber core to grow a crystalline cladding layer thereon comprises holding the crystalline fiber core in the molten LPE solution by a holder to minimize thermally induced stress. The holding step is conducted by a method selected from the group consisting of pre-bent holding technique or one-end firm holding and other end or parts loose holding technique as well as mesh-type bottom support to enhance the strength of holding while allowing molten flux passing through the mesh-type support to achieve a uniform cladding. In one embodiment, multiple working techniques are utilized to minimize thermally induced stress to the crystalline fiber core.

In one embodiment of the method, prior to the cladding growing step, a crystalline fiber core preform is immersed into an under-saturated LPE flux to form the crystalline fiber core having a diameter smaller than the diameter of the crystalline fiber core preform, and the cladding growing step comprises immersing the crystalline fiber core into a super-saturated LPE flux with cladding composition to grow a crystalline cladding layer onto the crystalline fiber core and the refractive index of the crystalline cladding layer is different from the crystalline fiber core (e.g., lower than the refractive index of crystalline fiber core).

In one embodiment of the method, the container is made from a material selected from the group consisting of platinum (Pt), platinum-gold (Pt—Au) alloys, platinum-rhodium (Pt—Rh) alloys, iridium (Ir), platinum-iridium (Pt—Ir) alloys, dispersion-hardened platinum, and dispersion-hardened platinum alloys.

In one embodiment of the method, the fiber holder or crucible moves linearly back and forth along an axial direction of the crystalline fiber core, or the fiber holder or crucible moves linearly back and forth along the direction perpendicular to the axial direction of crystalline fiber core, or the fiber holder or crucible rotates back and forth within an angle of motion of ±90° or a combination thereof. Moreover, the holder is made from a material selected from the group consisting of platinum (Pt), platinum-gold (Pt—Au) alloys, platinum-rhodium (Pt—Rh) alloys, iridium (Ir), platinum-iridium (Pt—Ir) alloys, dispersion-hardened platinum, and dispersion-hardened platinum alloys.

In one embodiment of the method, the molten LPE solution comprises $PbO-B_2O_3$, $BaO-B_2O_3-BaF_2$, $MoO_3-Li_2MoO_4$, and aqueous potassium carbonate (K2CO3).

In one embodiment of the method, multiple crystalline cladding-crystalline core optical fiber systems are formed simultaneously.

In one embodiment of the method, prior to or concurrently with immersing the crystalline fiber core preform into the under-saturated LPE flux, reducing the diameter of the crystalline fiber core preform by a method of, for example, lapping and polishing crystalline fiber core preform by moving the crystalline fiber core preform in a lapping and polishing solution comprising diamond, alumina, boron carbide, silicon carbide, colloidal silica, or other lapping/polishing powders, or etching crystalline fiber core preform using hot orthophosphoric acid $H_3PO_4$, hot hydrofluoric acid (HF), hot sulfuric acid ($H_2SO_4$), or a combination thereof, or subsequent to forming the crystalline fiber core but prior to the cladding growing step, reducing the diameter of the crystalline fiber core by a method selected from the group consisting of lapping and polishing crystalline fiber core by moving the crystalline fiber core preform in a lapping and polishing solution comprising diamond, alumina, boron carbide, silicon carbide, colloidal silica, or other lapping/polishing powders, or etching crystalline fiber core preform using hot orthophosphoric acid $H_3PO_4$, hot hydrofluoric acid (HF), hot sulfuric acid ($H_2SO_4$), or a combination thereof.

In another embodiment, a crystalline cladding-crystalline fiber core optical system is formed by contacting a molten liquid phase epitaxy (LPE) solution with a crystalline fiber core to grow a crystalline cladding layer thereon, wherein the refractive index of the crystalline cladding layer is lower than the refractive index of the crystalline fiber core.

In one embodiment, the crystalline cladding and/or the crystalline fiber core of the crystalline cladding-crystalline fiber core optical system contain $(Y_{1-x-y-z},Gd_x,Lu_y,Tb_z)_3(Al_{1-w},Ga_w)_5O_{12}$, where x, y, z, and w are within the range of 0 to 1.

In one embodiment, the crystalline cladding and/or the crystalline fiber core of the crystalline cladding-crystalline core fiber optical system contain dopants selected from the group consisting of erbium, ytterbium, neodymium, thulium, holmium, chromium, cerium, samarium, dysprosium, terbium, titanium, vanadium, magnesium, manganese, iron, cobalt, nickel, copper, bismuth, and combinations thereof.

In one embodiment, the crystalline cladding and crystalline core fiber optical system contain materials selected from the group consisting of pure and/or doped yttrium lithium fluoride (YLF), pure and/or doped yttrium orthovanadate (YVO4), pure and/or doped gadolinium orthovanadate (GdVO$_4$), pure and/or doped colquiriite (LiSaF), pure and/or doped alumina ($Al_2O_3$), pure and/or doped spinel ($MgAl_2O_4$), pure and/or doped aluminum oxynitride (AlON), pure and/or doped yttria ($Y_2O_3$), pure and/or doped zirconia ($ZrO_2$), pure and/or doped aluminum nitride (AlN), pure and/or doped yttrium iron garnet (YIG), pure and/or doped potassium tantalate niobate (KTN), pure and/or doped lithium niobate ($LiNbO_3$), pure and/or doped tantalate niobate ($LiTaO_3$), pure and/or doped lanthanum lead zirconate-titanate (PLZT), pure and/or doped lead magnesium niobate-lead titanate (PMN-PT), and combinations thereof.

In one embodiment, the fiber has multiple cladding layers consisting of an outer (crystalline or amorphous) cladding and an inner crystalline cladding, wherein the refractive index of the outer cladding is lower than the refractive index of the inner crystalline cladding. In one embodiment, an outer metal layer overlays the outer cladding, wherein the outer metal layer is selected from the group consisting of but not limited to silver, aluminum, copper, gold, platinum, titanium, nickel, chromium, and combinations thereof.

In one embodiment, a device comprises the crystalline cladding-crystalline core fiber optical system formed by contacting a molten liquid phase epitaxy (LPE) solution with a crystalline fiber core to grow a crystalline cladding layer thereon, wherein the refractive index of the crystalline cladding layer is lower than the refractive index of the crystalline fiber core, and further wherein the device is selected from the group consisting of fiber lasers, fiber amplifiers, fiber optic sensors, and all-fiber optical isolators.

U.S. patent application Ser. No. 15/220,807, incorporated by reference herein, reports a method and apparatus for producing crystalline cladding and crystalline core optical fibers, including the thermal stress free holding of the crystalline fiber seed during the etching process by applying an under-saturated liquid solution and growing process by applying a super-saturated solution.

Several thermal stress free holding methods have been reported in the patent application Ser. No. 15/220,807. Although this described holding method can provide the thermal stress free holding improvements in control of the shape of held fiber remain possible. Since crystalline fiber is very fragile and flexible (i.e., very bendable), in particular when the diameter of the fiber core is thin (e.g., ≤100 µm), it is useful not only to hold fiber without the thermal stress but also to control the shape of the fiber seed without much bending. For example, when a vertical temperature gradient is applied on a furnace to enable crystal growth in liquid solutions, it is important to hold the fiber near a straight horizontal line so that the fiber encounters the same etching and growth temperatures. This ensures a uniform fiber core and fiber cladding along the fiber axial directions.

To possibly assist with this goal, we report a growing method and apparatus, which can not only provide a thermal stress free holding but also control the shape of the fiber without much bending during the etching and growing process. Furthermore, it also provides a way to easily separate the grown crystalline fiber and holder after the growth so that the fiber will not be bonded on the holder. Thus, the fiber will not be broken by the thermal stress due to the different thermal expansion coefficients between the fiber and the holder.

To enable that a grown fiber has a desired geometry, such as the diameter of core and diameter of the cladding, it is important to constantly monitor the fiber (such as measuring the diameter of the fiber) during the growing process. Existing methods have relied on measuring the reflected image, which suffers severe limitations for monitoring the growth of crystalline core and crystalline cladding fiber. For example, the contrast ratio of the detected reflection image can be very poor when the refractive index difference between the being grown crystalline fiber and surround flux is small. For instance, the refractive index of rare earth doped yttrium aluminum garnet (YAG) is around $n_{YAG}=1.82$ and the refractive index of the lithium molybdate ($Li_2MoO_4$) based flux is around $n_{LM}=1.78$. In this case, the reflectivity, R, at the boundary between YAG and flux under normal incidence angle is given by $$R = \frac{(n_{YAG} - n_{LM})^2}{(n_{YAG} + n_{LM})^2} = 1.2 \times 10^{-4}. \quad (1)$$

Such a small reflectivity makes it extremely difficult form a clear high contrast image of the being grown crystalline, in particular for the small diameter crystalline fiber. To overcome this limitation, we propose to use the absorption image and fluorescent image to monitor the crystalline fiber growing process.

DETAILED DESCRIPTION OF THE INVENTION

Figure 1:
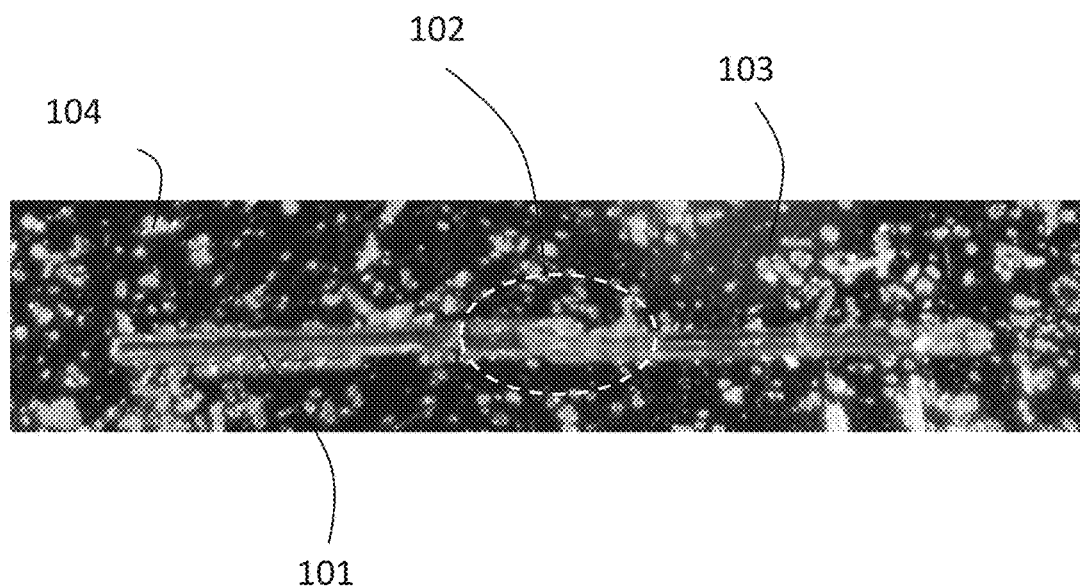
FIG. 1 shows a picture of crystalline YAG fiber 101 that was broken in the area 102 caused by the thermal stress generated during the cooling off process because the fiber 101 was bonded together with the platinum (Pt) holder 103 by the residual flux 104.

In the following detailed description, numerous specific embodiments are set forth to provide a thorough understanding of the apparatus and methods disclosed herein. However, as will be apparent to those skilled in the art, the present embodiments may be practiced without these specific details or by using alternate elements or processes. Embodiments as reported herein may also be combined with each other. In other instances, well-known processes, procedures, and/or components have not been described in detail so as not to unnecessarily obscure aspects of embodiments disclosed herein. As used herein in connection with numerical values the term "about" refers to ±10%.

I. Liquid Phase Epitaxy (LPE)

Embodiments as reported herein may provide methods and apparatus for preparing a crystalline cladding-crystalline core fiber optical system through liquid phase epitaxy (LPE). LPE is a method for growth of crystalline layers from a supersaturated liquid solution (flux) onto a crystalline substrate, including following steps: (1) solution is prepared and supersaturated at a temperature $T_1$, (2) substrate is brought into the contact with supersaturated solution, and (3) crystalline layer is grown on the crystalline substrate. The supersaturated flux can be achieved by cooling a saturated solution or creating a temperature gradient in which the crystalline substrate seed locates at an area that has a temperature lower than that of source area.

Although LPE is useful for crystalline layer growth on rigid planar substrate materials, thus far investigators have found it less useful for grown of crystalline cladding on thin, long fiber cores that might function in fiber lasers and fiber sensors. Unlike a rigid crystalline wafer, thin and long crystalline fiber cores are very fragile and flexible and cannot be easily held in LPE solution by known methods, including for example use of a platinum tricep.

Typically fibers as reported herein are characterized as long and thin fibers. Although not limiting upon the claims unless so stated therein, a "thin" fiber typically has a core diameter from approximately 1 micron to approximately 150 microns and a "long" fiber typically has a length of at least approximately 5 cm.

In embodiments of the invention the refractive index of crystalline cladding is (0.01% to 10%) lower than that of crystalline core; the diameter of crystalline core is within the range of 1 micron to 150 microns, preferably 10 microns to 100 microns; the thickness of crystalline cladding layer is within the range of 1 micron to 1,000 microns, preferably 10 microns to 500 microns; and the length of crystalline cladding and crystalline core fiber is within the range of 1 cm to 10,000 cm, preferably 10 cm and longer.

In various embodiments of the invention, the fiber core may be, for example, pure and/or doped garnet $(Y_{1-x-y-z}, Gd_x, Lu_y, Tb_z)_3(Al_{1-w}, Ga_w)_5O_{12}$, where x, y, z, and w are within the range of 0 to 1, pure and/or doped yttrium lithium fluoride (YLF), pure and/or doped yttrium orthovanadate ($YVO_4$), pure and/or doped gadolinium orthovanadate ($GdVO_4$), pure and/or doped colquiriite (LiSaF), pure and/or doped alumina ($Al_2O_3$), pure and/or doped spinel ($MgAl_2O_4$), pure and/or doped aluminum oxynitride (AlON), pure and/or doped yttria ($Y_2O_3$), pure and/or doped zirconia ($ZrO_2$), pure and/or doped aluminum nitride (AlN), pure and/or doped yttrium iron garnet (YIG), pure and/or doped potassium tantalate niobate (KTN), pure and/or doped lithium niobate ($LiNbO_3$), pure and/or doped tantalate niobate ($LiTaO_3$), pure and/or doped lanthanum lead zirconate-titanate (PLZT), pure and/or doped lead magnesium niobate-lead titanate (PMN-PT), gallium arsenide (GaAs), gallium aluminum arsenide (GaAlAs), gallium nitride (GaN) and combinations thereof. The cladding may be, for example, pure and/or doped garnet $(Y_{1-x-y-z}, Gd_x, Lu_y, Tb_z)_3(Al_{1-w}, Ga_w)_5O_{12}$, where x, y, z, and w are within the range of 0 to 1, pure and/or doped yttrium lithium fluoride (YLF), pure and/or doped yttrium orthovanadate ($YVO_4$), pure and/or doped gadolinium orthovanadate ($GdVO_4$), pure and/or doped colquiriite (LiSaF), pure and/or doped alumina ($Al_2O_3$), pure and/or doped spinel ($MgAl_2O_4$), pure and/or doped aluminum oxynitride (AlON), pure and/or doped yttria ($Y_2O_3$), pure and/or doped zirconia ($ZrO_2$), pure and/or doped aluminum nitride (AlN), pure and/or doped yttrium iron garnet (YIG), pure and/or doped potassium tantalate niobate (KTN), pure and/or doped lithium niobate ($LiNbO_3$), pure and/or doped tantalate niobate ($LiTaO_3$), pure and/or doped lanthanum lead zirconate-titanate (PLZT), pure and/or doped lead magnesium niobate-lead titanate (PMN-PT), gallium arsenide (GaAs), gallium aluminum arsenide (GaAlAs), gallium nitride (GaN) and combinations thereof. The dopants for the core and/or cladding can be selected from the group consisting of aluminum, erbium, ytterbium, neodymium, thulium, holmium, chromium, cerium, samarium, dysprosium, terbium, titanium, vanadium, magnesium, manganese, iron, cobalt, nickel, copper, bismuth, and combinations thereof.

A. Preparation of Crystal and Use of a Holder

Attempts at preparing a thin and long crystalline fiber core in a holder have previously been unsuccessful. Unlike what is effective for rigid crystalline wafers, the adhered flux cannot be spun off by raising the substrate above the melt surface and rotating it at high speed (for example, greater than 300 rpm) and at high flux melting temperature because high speed rotation would break the fragile thin and long fiber core.

Typically a crystalline core is prepared prior to cladding of that core. A crystalline core may be prepared, for example, by one of a laser heated pedestal growth (LHPG) method, micro-pulling, and an edge-defined film-fed growth (EFG) method.

Prior LPE attempts to clad such cores have been unsuitable for many reasons. For example, adhered flux can bond crystalline fiber core and the holder together during the cooling off solidification process. This can break the fiber core due to differences in thermal expansion coefficient (TEC) of holder and the crystalline fiber core. For example, TEC of a platinum holder is about $9 \times 10^{-6}$/K while TEC of yttrium aluminum garnet (YAG) crystalline fiber core is about $6.14 \times 10^{-6}$/K. Such a difference in TEC generates thermally induced stress that can weaken and break the fiber core during the cooling off process. The thermally induced stress increases with axial length of the crystalline fiber core. For example, FIG. 1 illustrates a crystalline YAG fiber core 101 that has broken in area 102 during the cooling off process due to thermally induced stress caused by bonding crystalline fiber core 101 with a platinum holder 103 via residual flux 104.

Figure 2:
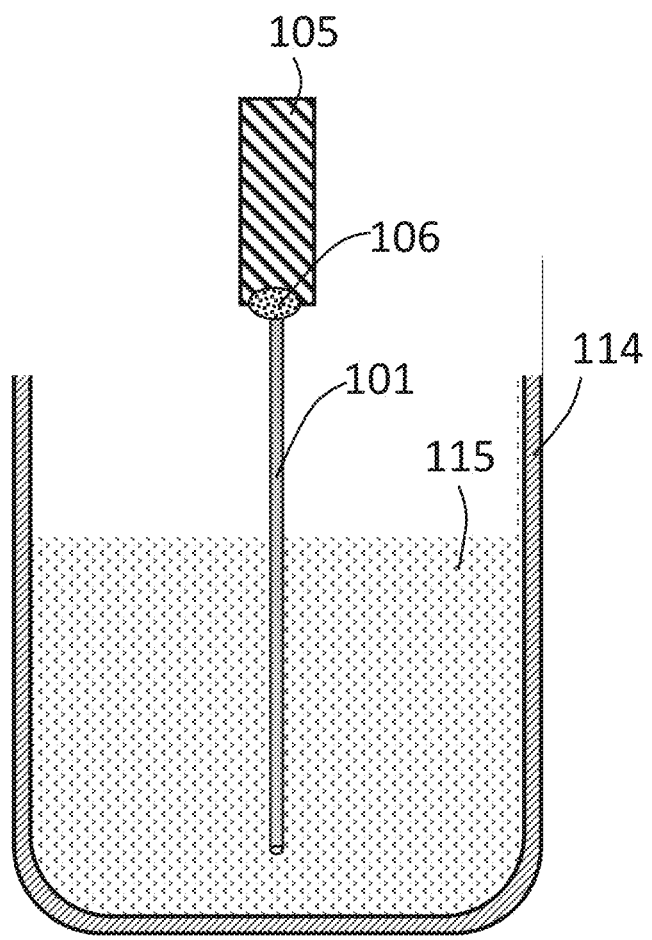
FIG. 2 shows an illustration of vertically holding a crystalline fiber 101 in a molten flux 115, consisting of a crystalline fiber 101, a molten flux 115, a crucible 114, a rigid holder 105, and a high temperature holding component (e.g., a high temperature adhesive) 106.

Although the issue of thermally induced stress may be alleviated by vertically holding the crystalline fiber (e.g., by high temperature adhesive 106) and dipping it into a molten flux, as illustrated in FIG. 2, it is very difficult to achieve a uniform crystalline cladding growth on the crystalline fiber core along the fiber due to the existence of thermal convection and the fluid flux motion caused by density changes in the layer of liquid next to the growing interface [J. M. Robertson, Liquid phase epitaxy of garnets, J. of Crystal growth 45 pp. 233-242, 1978]. Thus, horizontally holding the fiber in a molten flux is preferred. However, the previously reported LPE horizontally holding method is only suitable for holding rigid crystalline wafer but not for the fragile and flexible crystalline fiber core. For example, unlike horizontally holding a rigid crystalline wafer substrate, one cannot horizontally hold a crystalline fiber by holding just one end because the fiber is flexible.

Figure 3:
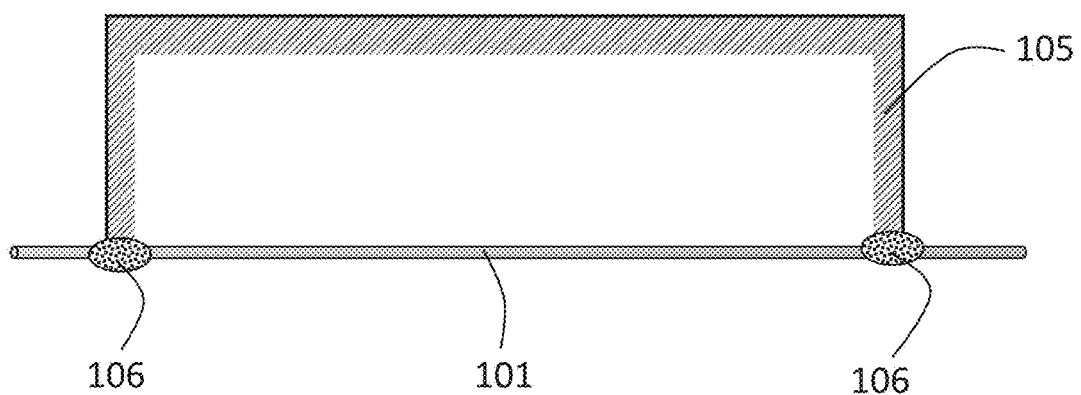
FIG. 3 shows an illustration of an improper method of holding a crystalline fiber 101 in straight by fixing both ends of fiber on a rigid holder 105 (e.g., by using high temperature adhesive 106) that can break the fiber due to the thermally induced stress.

Furthermore, unlike holding a rigid crystalline wafer substrate, the crystalline fiber core 101 cannot be horizontally held straight by fixing both ends of the crystalline fiber core 101 on a rigid holder 105 (for example, by using a high temperature adhesive 106), as illustrated in FIG. 3. Because of differences in TEC between the crystalline fiber core and rigid holder and the very fragile nature of thin and long crystalline fiber, the crystalline fiber can be damaged by thermal stresses generated during temperature ramp-up and/ or cooling down in LPE growth. Thus, it is critical to develop proper holding methods which overcome thermal stress problems associated with thin, long crystalline fiber cores.

Figure 4:
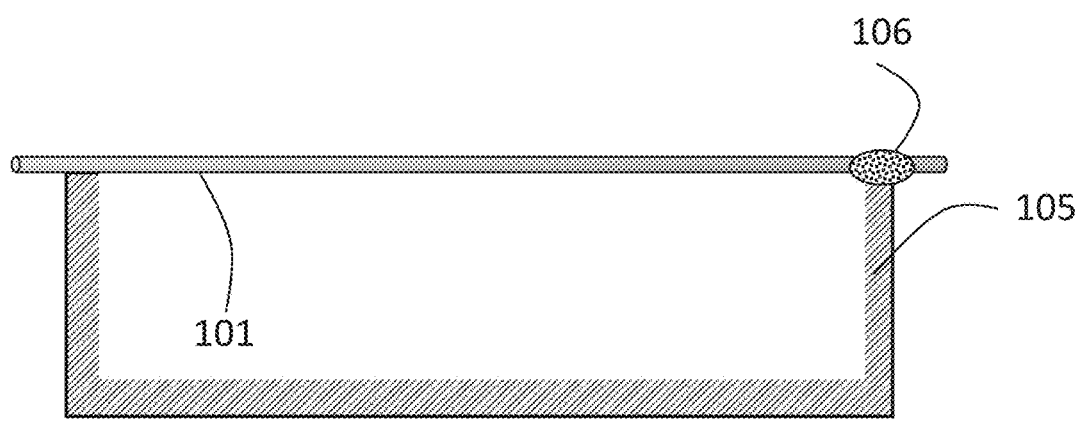
FIG. 4 shows an illustration of a proper method of holding a crystalline fiber core preform 101 in a holder 105 taught by the present invention, in which one of the fiber is firmly fixed on the holder 105 (e.g., by using a high temperature adhesive 106) whereas the other end of fiber can move freely at least in the axial direction so that there will be no or reduced thermally induced stress during the temperature ramp-up and cooling off process.

FIG. 4 illustrates a method of attaching the crystalline fiber core 101 on a holder 105 to properly hold (i.e. with no or reduced thermally induced stress) the crystalline fiber core horizontally in the LPE growing process according to an embodiment of the invention. In this embodiment, one end of the crystalline fiber core is firmly fixed on the holder while a second end moves freely in at least the axial direction.

This axial movement may be permitted, for example, by providing a hole in the second end of holder. The fiber core can pass through the hole. Since the second end of fiber core can move freely in at least the axial direction, it does not generate thermally-induced stresses during temperature ramp-up and/or cooling down during the LPE growing process. This minimizes damage induced by thermal stress.

Figure 5A:
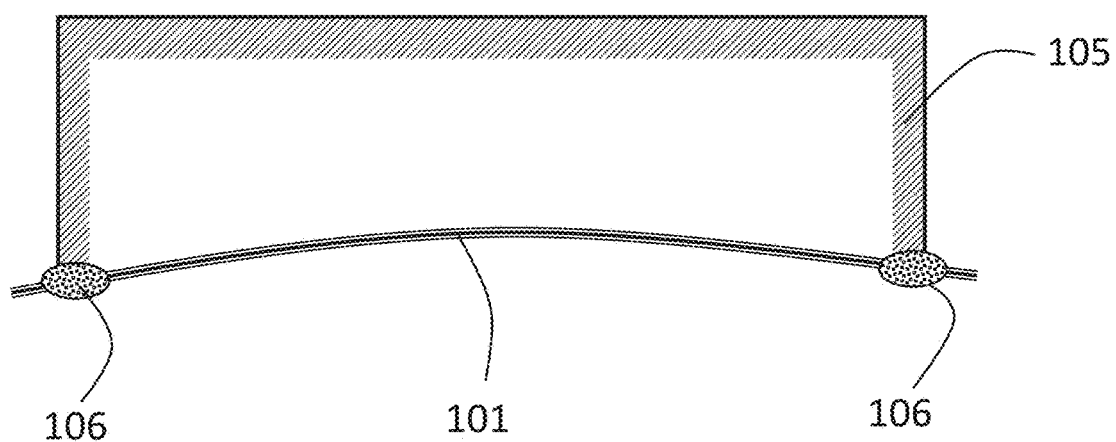
FIG. 5A shows an illustration of another proper method of holding a crystalline fiber core preform 101 in a holder 105 taught by the present invention, in which there is a pre-bent on the fiber although both ends of fiber are firmly fixed on an upper holder. Such a bend can release or reduce the thermally induced stress during the temperature ramp up and/or cooling off in the LPE growing process caused by the difference in thermal expansion coefficients between the crystalline fiber core and the holder.
Figure 5B:
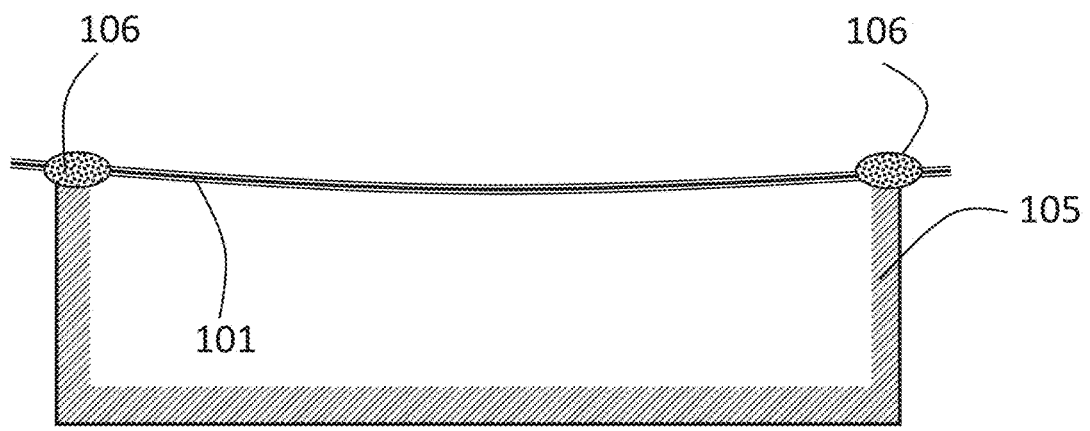
FIG. 5B shows an illustration of another proper method of holding a crystalline fiber core preform 101 in a holder 105 taught by the present invention, in which there is a pre-bent on the fiber although both ends of fiber are firmly fixed on a lower holder. Such a bend can release or reduce the thermally induced stress during the temperature ramp up and/or cooling off in the LPE growing process caused by the difference in thermal expansion coefficients between the crystalline fiber core and the holder.

FIGS. 5A and 5B illustrate another embodiment for attaching the crystalline fiber core 101 on holder 105. In this embodiment both ends of the fiber core are firmly fixed on the holder 105. However, bending the fiber core 101 prior to the LPE process releases or reduces the thermally-induced stress during temperature ramp up and/or cool-down caused by the difference in TEC between the crystalline fiber core 101 and the holder 105.

Figure 5C:
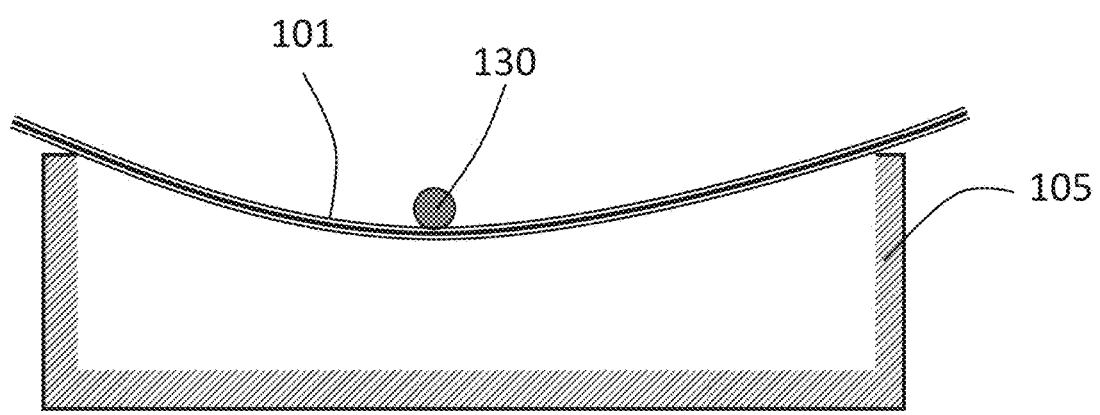
FIGS. 5C and 5D illustrate holding a pre-bend fiber core 101 with a central fixture 130.
Figure 5D:
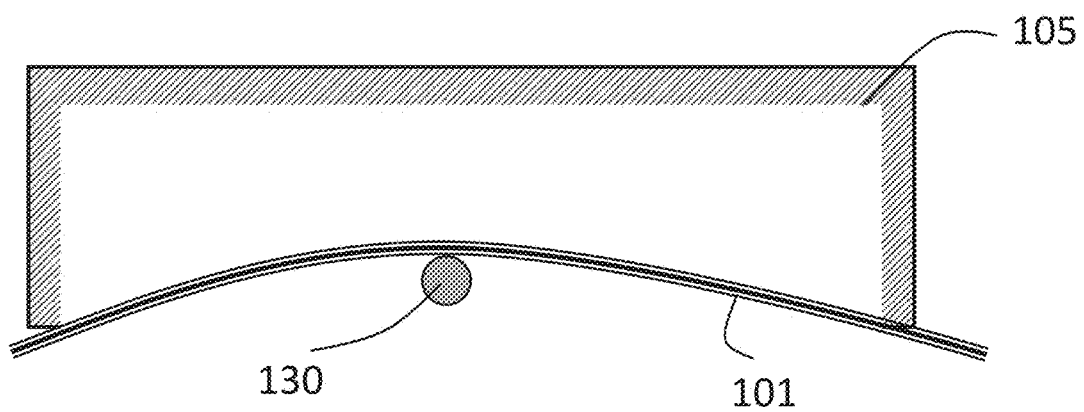

FIGS. 5C and 5D illustrate hold the fiber 101 with a central fixture 130 to reduce the thermal stress. In this embodiment, the firm fix on both ends of fiber may not be needed.

Figure 5E:
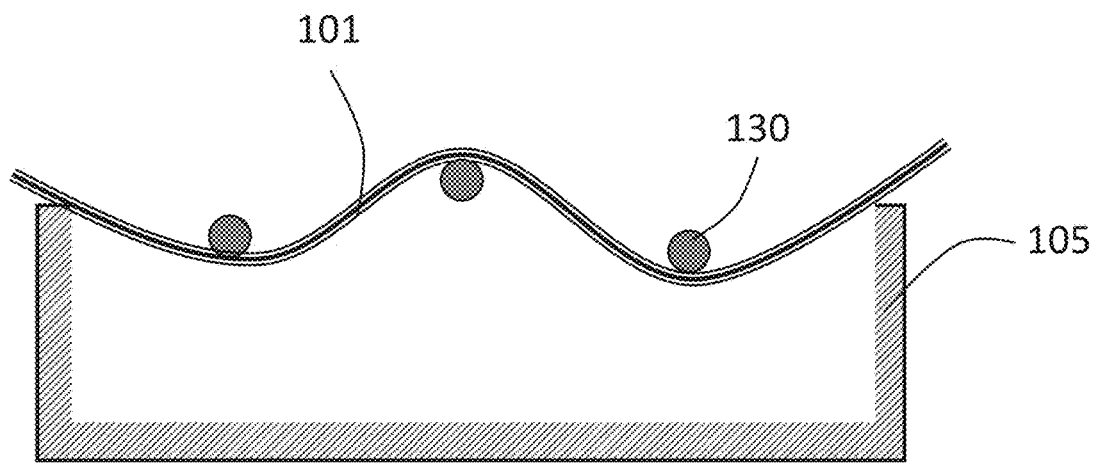
FIGS. 5E and 5F illustrate holding a fiber core 101 with multiple pre-bends by multiple fixtures 130.
Figure 5F:
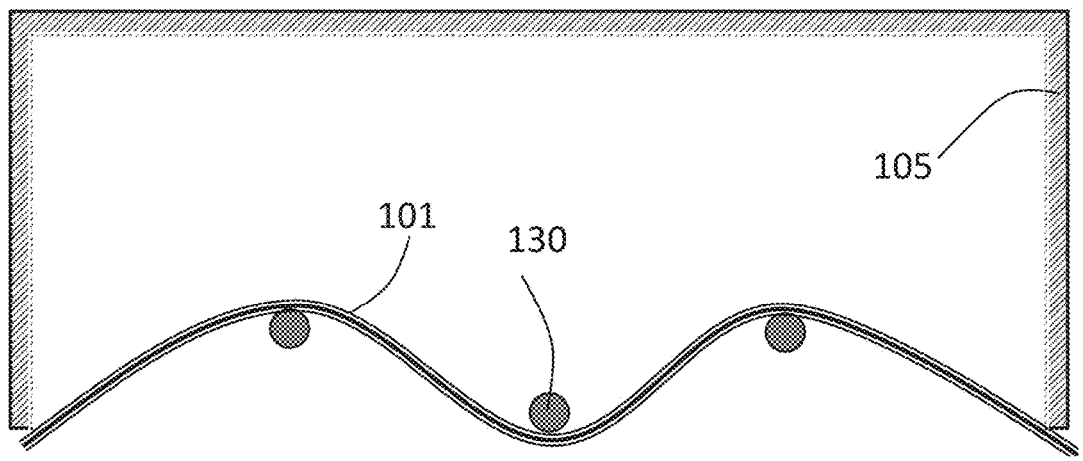

FIGS. 5E and 5F illustrate hold the fiber 101 with multiple pre-bends by multiple fixtures 130 to reduce the thermal stress. Again, in this embodiment, the firm fix on both ends of fiber may not be needed.

Figure 5G:
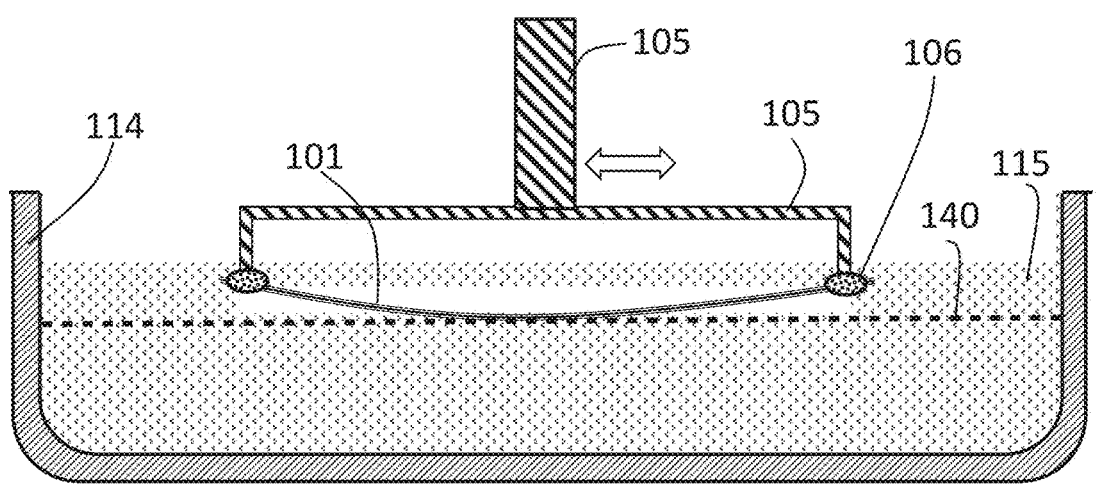
FIG. 5G illustrates another method of holding a crystalline fiber core preform 101 in a holder 105 including a 1-dimensional (1D) or 2-dimensional (2D) mesh-type bottom support 140 that enhances the strength of holding thin and long crystalline fiber core preform.

FIG. 5G shows an illustration of another method of holding a crystalline fiber core preform 101 in a holder 105 including a 1-dimensional (1D) or 2-dimensional (2D) mesh-type bottom support 140 that enhances the strength of holding thin and long fiber core preform. The mesh-type support 140 and crucible 114 are attached together. The molten flux can pass through the mesh type support. Both the fiber core preform 101 and the mesh support are immersed in the molten flux 115 and there is a relative movement between the fiber 101 and mesh-type support 140 in at least fiber axial direction during the LPE growing process, which ensures a uniform cladding growth along the fiber core.

Figure 6:
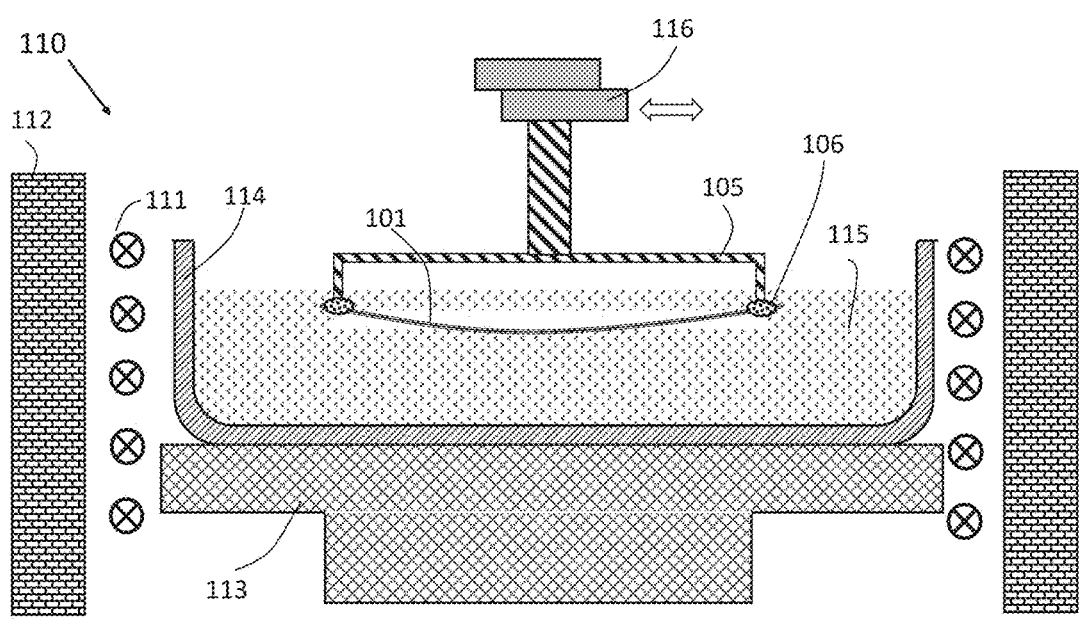
FIG. 6 shows an illustration of a LPE system 110 used to grow the crystalline cladding and crystalline core optical fiber taught by the present invention, which is comprised of (1) a heating element 111 and insulator 112 that can produce the required temperature and temperature distribution for properly melting the LPE flux, (2) a pedestal 113 to hold the growing crucible, (3) a crucible 114, (4) LPE flux 115, (5) a properly held (i.e. with no or reduced thermally induced stress) crystalline fiber core preform 101 that is immersed in the molten LPE flux, and (6) a moving stage 116.

FIG. 6 illustrates an LPE-grown crystalline cladding-crystalline core fiber system 110 used to grow the crystalline cladding upon a crystalline optical fiber core in an embodiment as reported herein. The system includes (1) a heating element 111 and corresponding thermal insulator 112, which produces the required temperature (from about 800° C. to about 1350° C. for fluxes including but not limited to lead oxide-boron trioxide mixture ($PbO—B_2O_3$), a barium oxide-boric oxide-barium fluoride mixture ($BaO—B_2O_3—BaF_2$), a molybdenum oxide-lithium molybdate mixture ($MoO_3—Li_2MoO_4$), lithium oxide-molybdenum oxide ($Li_2O—MoO_3$) and from about 500° C. to about 1000° C. for flux including but not limited to aqueous potassium carbonate ($K_2CO_3$) and temperature distribution profile (uniform and/ or a temperature gradient within the range of 0.1° C./cm to 100° C./cm) for properly melting the LPE flux; (2) a pedestal 113 to hold a growing crucible 114; (3) a crucible 114; (4) an LPE flux 115; and (5) a held crystalline fiber core 101 that is immersed into a molten LPE flux 115. The crystalline fiber core 101 is held with no or reduced thermal stress (i.e. properly held) by the methods as illustrated in FIGS. 4, 5A-5G.

In a typical embodiment the holder used to hold the crystalline fiber core is attached to a moving stage and controller 116. This enables the holder to move during the LPE growth process. Or, the holder does not move and the crucible moves. Or, both the holder and crucible move.

The system includes a heating element. The heating element may be, for example, but is not limited to a resistant heating wire, silicon carbide (SiC) heater, platinum (Pt) wire heater, Pt-alloy wire heater, molybdenum disilicide (MoSi2), and combinations thereof. Other types of heating methods may also be employed, either alone or in combination with the heating elements. These include, for example, but are not limited to radio frequency (RF) heating and microwave heating.

The crucible material is selected so that it does not react with the LPE flux. Crucible materials may include, for example, but are not limited to platinum and platinum alloys.

Various crucible shapes may be used. To cost-effectively grow the crystalline cladding on the thin, long crystalline fiber core, the crucible shape typically matches the shape of thin, long crystalline fiber core. This may be, for example, a rectangular, trough-shaped, or boat-shaped crucible.

Crucible size may be minimized by permitting the holder to move linearly along an axial direction of the crystalline fiber core. Crucible size may also be minimized if the holder is permitted to rotate back and forth within an angle of motion of ±90° relative to the fiber core axis. Combinations of linear motion and rotation may also be used.

B. Flux and Growth Processes

A variety of fluxes may be employed in the LPE growing process. These include, for example, but are not limited to a lead oxide-boron trioxide mixture ($PbO$—$B_2O_3$), a barium oxide-boric oxide-barium fluoride mixture ($BaO$—$B_2O_3$—$BaF_2$), a molybdenum oxide-lithium molybdate mixture ($MoO_3$—$Li_2MoO_4$), a lead oxide-boron trioxide-lead fluoride mixture ($PbO$—$PbF_2$—$B_2O_3$), a lead oxide-vanadium pentoxide mixture ($PbO$—$V_2O_5$), a molybdenum oxide-potassium fluoride mixture ($KF$—$MoO_3$), a potassium fluoride-barium titanate mixture ($KF$—$BaTiO_3$), an aqueous potassium carbonate ($K_2CO_3$), a lead oxide-lead fluoride mixture ($PbO$—$PbF_2$), a lead fluoride-boron trioxide mixture ($PbF_2$—$B_2O_3$), a lithium oxide-molybdenum oxide mixture ($Li_2O$—$MoO_3$), a lead oxide-bismuth oxide mixture ($PbO$—$Bi_2O_3$), and a molybdenum oxide-potassium molybdate-yttria mixture ($MoO_3$—$K_2MoO_4$—$Y_2O_3$).

Cladding growth ingredients are mixed with flux in an LPE process. For example, in order to grow crystalline YAG cladding layer, yttria ($Y_2O_3$) and alumina ($Al_2O_3$) powders are mixed with the powders of the fluxes. In addition to yttria and alumina, other materials (such as gallium oxide ($Ga_2O_3$), ytterbium oxide ($Yb_2O_3$), neodymium oxide ($Nd_2O_3$), lutetium oxide ($Lu_2O_3$), erbium oxide ($Er_2O_3$), terbium oxide ($Tb_2O_3$), gadolinium oxide ($Gd_2O_3$), and their combinations thereof) may also mix with the powders of fluxes to change the properties of the grown crystalline cladding layer (i.e. refractive index, light emission, light absorption). As another example, by dissolving alumina powder in the flux, sapphire cladding layer can be grown.

The identity of the cladding growth ingredients and the flux will determine the ultimate composition of the cladding. For example, by dissolving yttria ($Y_2O_3$) and alumina ($Al_2O_3$) powders in lead oxide-boron trioxide ($PbO$—$B_2O_3$) flux, or a barium oxide-boric oxide-barium fluoride ($BaO$—$B_2O_3$—$BaF_2$) flux, or a molybdenum oxide-lithium molybdate mixture ($MoO_3$—$Li_2MoO_4$) flux, or a lead oxide-boron trioxide-lead fluoride ($PbO$—$PbF_2$—$B_2O_3$) flux, or a lead oxide-lead fluoride ($PbO$—$PbF_2$) flux, or a lead fluoride-boron trioxide ($PbF_2$—$B_2O_3$) flux, crystalline YAG can be grown. As another example, by dissolving alumina ($Al_2O_3$) in lithium oxide-molybdenum oxide ($Li_2O$—$MoO_3$) flux, a sapphire crystal can be grown.

A typical LPE growth process includes following steps: (1) mixing flux ingredients and cladding growth ingredients, typically as powders, (2) placing the mixed powders inside a crucible 114; (3) heating the mixed powders to an elevated melting temperature, which is high enough to melt the flux and dissolve the cladding growth ingredients into the flux but lower than the boiling point of the flux for minimizing flux volatilization, to form a melted flux; (4) if necessary, cooling the flux/growth ingredient mixture from saturation temperature to form super-saturated molten flux; for example to grow YAG in a $PbO$—$B_2O_3$ based flux, $Y_2O_3$ and $Al_2O_3$ powders are dissolved in the $PbO$—$B_2O_3$ flux at about 1050° C. and maintained at that temperature for a considerable amount of time (e.g. approximately 15 hrs) to reach a homogeneous saturation solution. Then, the supersaturation is realized by cooling the flux from about 1050° C. to about 940° C. As another example, for a $MoO_3$—$Li_2MoO_4$ based flux, due to the low solubility of the flux (e.g., 0.5 mole % at 1100° C. for YAG material), supersaturated flux is created through a suitable temperature gradient (for example, 5-20° C./cm) along the vertical direction of the crucible, which constantly transports source materials from the higher temperature bottom of the crucible to the crystalline fiber core; (5) immersing a held crystalline fiber core 101 with no or reduced thermal stress holding into a supersaturated molten flux 115; (6) growing crystalline cladding on the thin, long crystalline fiber core, including linear movement of the core along an axial direction of the crystalline fiber core; and (7) pulling out the crystalline cladding-crystalline core optical fiber from the crucible after growth while the flux is at the molten status. This allows it to be automatically detached from the crucible.

Figure 7A:
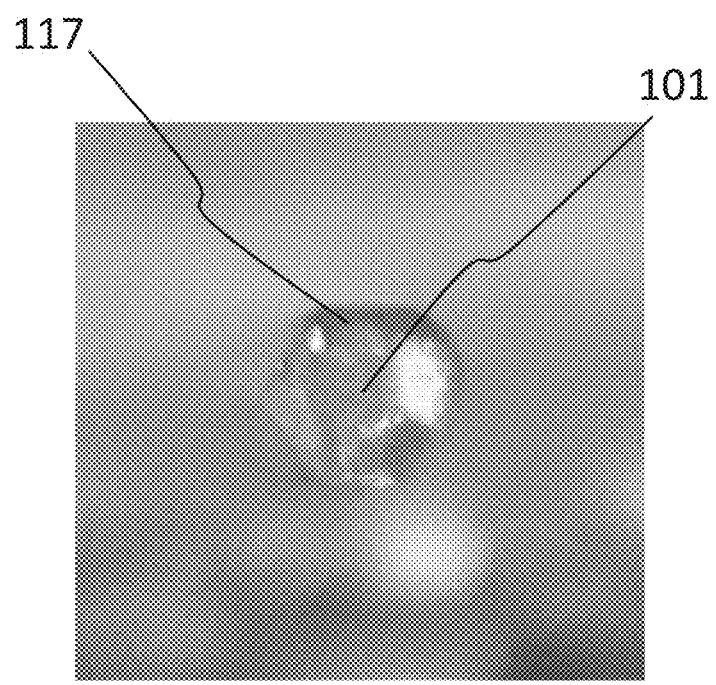
FIG. 7A shows a picture of an end view of a grown crystalline cladding 117 (made of Cr/Nd doped YAG) and crystalline core 101 (also made of Cr/Nd doped YAG but with different concentrations) optical fiber.
Figure 7B:
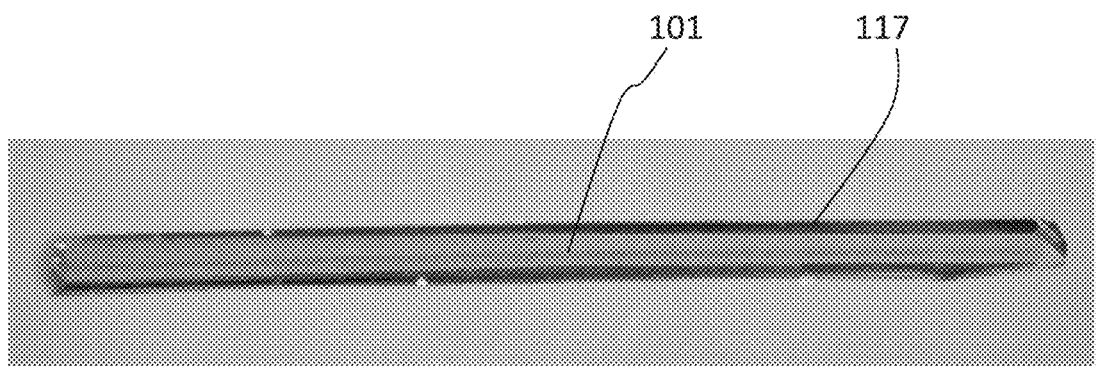
FIG. 7B shows a picture of a side view of a grown crystalline cladding 117 (made of Cr/Nd doped YAG) and crystalline core 101 (also made of Cr/Nd doped YAG but with different concentrations) optical fiber.

FIGS. 7A and 7B illustrate end and side views of a crystalline cladding-crystalline core optical fiber after growth of a chromium (Cr)— and neodymium (Nd)-doped YAG crystalline cladding atop a crystalline fiber core made from doped YAG. The thermal stress free (or reduced thermal stress) held crystalline YAG fiber core (as illustrated in FIGS. 4 and/or 5A-5G) was immersed into a $MoO_3$—$Li_2MoO_4$ based supersaturated flux, containing dissolved yttria and alumina powders, and the crystalline cladding was grown via an LPE growing process to form a crystalline doped YAG fiber core 101 and a crystalline doped YAG cladding layer 117. Unlike the prior art of FIG. 1, there are no breaks in crystalline cladding and crystalline core fiber by employing the thermal stress free (or reduced thermal stress) holding method taught in the present invention.

The thickness of the cladding layer may be controlled in multiple ways. For example, one might alter growing time, growing temperature, or growing temperature gradient of the grown solution. Variations in composition of the growth solution are also possible. For example, to grow YAG, a growth rate of about 0.1 to about 2 micron/min can be achieved by employing $PbO$—$B_2O_3$ flux and a growth rate of about 0.01 to about 0.2 micron/min can be obtained by harnessing $MoO_3$—$Li_2MoO_4$ flux. Thus, by growing YAG in $PbO$—$B_2O_3$ flux for approximately 100 minutes, a YAG cladding at least 10 microns thick can be achieved. By growing YAG in MoO$_3$—Li$_2$MoO$_4$ flux for approximately 1,000 minutes, a YAG cladding at least 10 microns thick can also be obtained.

C. Controlling Modes

To make an efficient fiber laser and/or fiber sensor, single or few mode clad crystalline fiber is preferred for its better-controlled transversal beam profile. Previously reported LPE-based crystalline film growing processes do not teach how to reduce and/or precisely control the number of modes propagated in the crystalline cladding and crystalline core optical fibers.

Embodiments reported herein report methods of reducing and/or precisely control the number of modes propagated in the crystalline cladding and crystalline core optical fibers. First, under-saturated flux is used to reduce the diameter of a crystalline fiber core preform. Subsequently, a super-saturated flux is applied to grow the crystalline cladding atop the reduced diameter crystalline fiber core that has a lower refractive index than that of fiber core.

Figure 8:
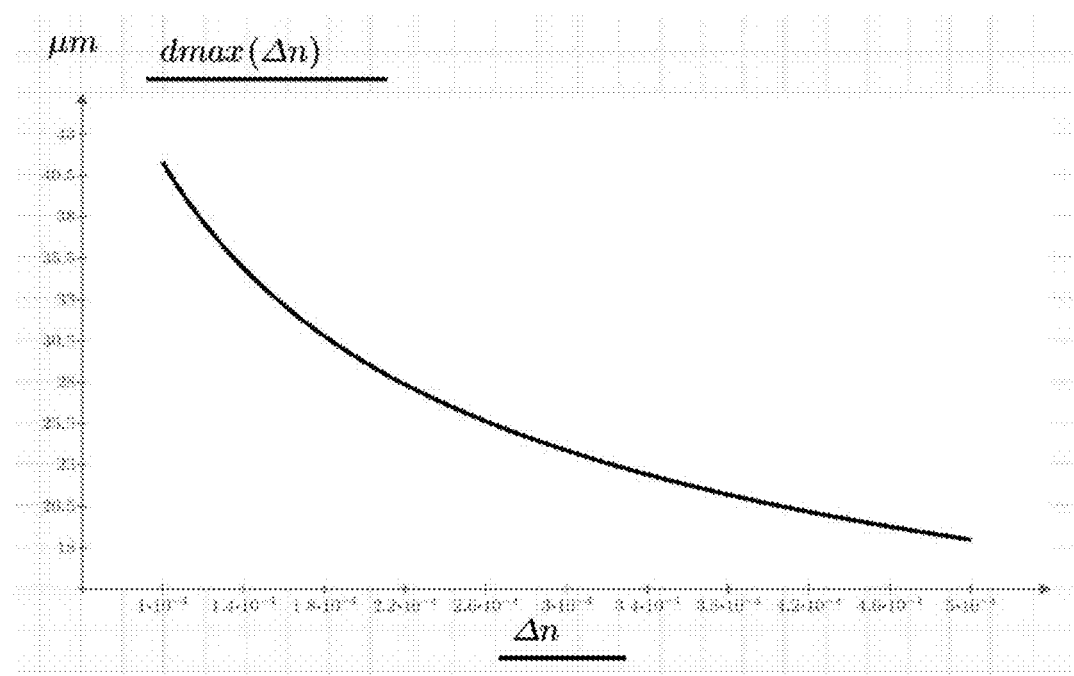
FIG. 8 shows the calculated maximum core diameter, $d_{max}$, for single mode operation as a function of refractive index difference, $\Delta n$, between a crystalline fiber core and a crystalline cladding at an operational wavelength of $\lambda=1030$ nm.

For a single mode crystalline fiber, a maximum core diameter, $d_{co-max}$, satisfies the following inequality $$d_{co-max} < \frac{2.405 \cdot \lambda}{\pi \cdot \sqrt{n_1^2 - n_2^2}}, \quad (1)$$

where $\lambda$ is the operational wavelength, and $n_1$ and $n_2$ denote the refractive indices of crystalline fiber core and crystalline cladding, respectively. FIG. 8 illustrates $d_{co-max}$ as a function of refractive index difference between crystalline fiber core and inner crystalline cladding $\Delta n = n_1 - n_2$. In the calculation, $n_1 = 1.82$ and $\lambda = 1.030$ μm (Yb:YAG lasing wavelength). $d_{co-max} \approx 20$ μm even for very small refractive index differences (for example, $\Delta n = 4 \times 10^{-4}$).

Refractive index differences between crystalline cladding and crystalline fiber core can be realized by doping. For example, the refractive index of a 4% Yb-doped YAG crystalline fiber core is approximately $4 \times 10^{-4}$ higher than the refractive index of pure crystalline YAG cladding. Current methods, including by laser heated pedestal growth (LHPG), are inadequate to grow long crystalline fiber core preforms (for examples, 1 meter) with small core diameters (for example, 20 μm). Although acid etching may be used to reduce the crystalline fiber core preform diameter, it can damage the surface and increases the scattering loss. To overcome these limitations, we provide an LPE process to reduce or precisely control the number of modes propagated in crystalline cladding and crystalline optical fiber core.

First, we provide an under-saturated LPE flux that reduces the diameter of the crystalline fiber core by dissolving a portion of the crystalline core into the flux. When under-saturated flux is used, the concentration levels of Y$_2$O$_3$ and Al$_2$O$_3$ dissolved in the flux are below their saturation levels. Thus, the material of crystalline YAG fiber core consisting of Y$_2$O$_3$ and Al$_2$O$_3$ are dissolved in the under-saturated flux such that the diameter of crystalline fiber core is reduced. For example, in one embodiment, when molybdenum oxide-lithium molybdate (MoO$_3$—Li$_2$MoO$_4$) flux is used to grow YAG crystal, the solubility of Y$_2$O$_3$ and Al$_2$O$_3$ is about 0.5 mole % at a temperature of 1050° C. When concentration levels of Y$_2$O$_3$ and Al$_2$O$_3$ are above 0.5 mole %, the flux is in a super-saturated state and can grow crystalline YAG thin film on crystalline YAG substrate. When concentration levels of Y$_2$O$_3$ and Al$_2$O$_3$ are below 0.5 mole %, the flux is in an under-saturated state. In an under-saturated state, Y$_2$O$_3$ and Al$_2$O$_3$ on the crystalline fiber core are dissolved into the flux, resulting in a thinned diameter of crystalline fiber core and a smoother surface relative to the original crystalline fiber core.

Subsequent to the under-saturated LPE flux treatment, the thinned core is treated through a super-saturated LPE flux. The supersaturated flux grows a crystalline cladding layer on the thinned crystalline fiber core. As an example of current invention, one can use two crucibles (or one crucible with two compartments) to realize this goal. One crucible (or one compartment) holds under-saturated flux and the other one holds super-saturated flux. The crystalline fiber core is first immersed in the under-saturated flux to reduce the core diameter and then immersed in the super-saturated flux to grow the crystalline cladding on the thinned crystalline fiber core. Furthermore, the material composition of super-saturated flux can be different from the under-saturated flux or crystalline fiber core so that the refractive index of grown crystalline cladding is different from the fiber core (e.g., lower than that of fiber core). For example, the crystalline fiber core preform may be Yb:YAG.

First, the Yb:YAG preform is immersed into an under-saturated flux that may contain Y$_2$O$_3$, Al$_2$O$_3$, or Yb$_2$O$_3$ at a concentration level less than the saturation level. Thus, the Y$_2$O$_3$, Al$_2$O$_3$, and Yb$_2$O$_3$ in fiber core preform are dissolved in the under-saturated flux so that the diameter of Yb:YAG preform is reduced. Then, the thinned Yb:YAG fiber core is immersed in the super-saturated flux. The super-saturated flux may only contain Y$_2$O$_3$ and Al$_2$O$_3$ but not Yb$_2$O$_3$. In this case, only pure YAG cladding is grown atop of Yb:YAG core. Since the refractive index of pure YAG is lower than that of Yb:YAG, the refractive index of crystalline cladding is lower than that of crystalline fiber core. Because the crystalline fiber core has a reduced diameter, the number of modes propagated in the crystalline cladding and crystalline core optical fiber are reduced. Alternatively, since saturation level is a function of temperature, one may use only one crucible to realize the goal. First, the flux is at saturation status at a temperature $T_2$. Second, we increase the temperature from $T_2$ to a higher temperature $T_3$ so that the flux is changed from saturation status to under-saturated status. The crystalline fiber core is immersed into the under-saturated flux at temperature $T_3$ for reducing the fiber core diameter. Third, the temperature of flux is reduced from $T_3$ to a lower temperature $T_t$ that is less than $T_2$. Flux becomes super-saturated so that cladding layer can be grown on the thinned fiber core at temperature $T_1$. An advantage of this approach is that it only needs one crucible or one compartment. However, it has less control on the composition as well as refractive index of crystalline cladding.

In one embodiment, the diameter of a Yb:YAG crystalline fiber core preform, grown by LHPG method, is reduced from about 100 μm to about 20 μm by immersing the preform into an under-saturated LPE flux. For example, in one embodiment, when the concentration of dissolved materials (i.e. Y$_2$O$_3$ and Al$_2$O$_3$) are below the saturation levels (i.e. <0.5 mole % for MoO$_3$—Li$_2$MoO$_4$ based flux at 1050° C.), the flux is under-saturated. Then, a pure YAG crystalline cladding is grown on this thinned diameter Yb:YAG crystalline fiber core, thus forming a single-mode crystalline cladding-crystalline fiber core optical system operating at a wavelength of 1030 nm.

Figure 9:
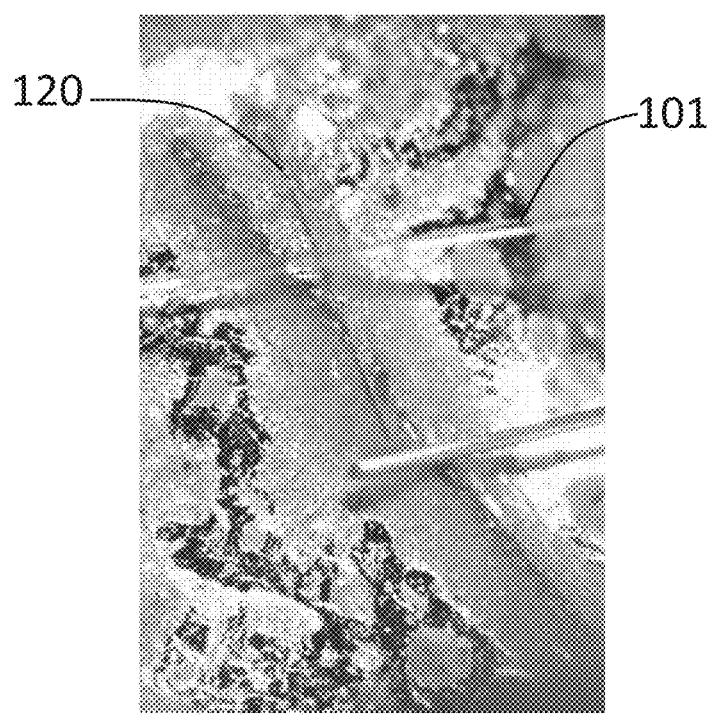
FIG. 9 shows a picture of single crystalline YAG fiber core with a thinned 20 μm diameter 120 by immersing a 100 μm crystalline YAG fiber core preform 101 into an undersaturated $MoO_3$—$Li_2MoO_4$ flux at 1100° C. for 3 hrs.

In one example, a single crystalline YAG fiber core preform with a diameter of approximately 100 μm was immersed in a MoO$_3$—Li$_2$MoO$_4$ under-saturated flux at a temperature of about 1100° C. for 3 hours. A thinned crystalline fiber core 120 having a smooth surface and a diameter of about 20 μm was formed, as shown in FIG. 9. Such diameters are sufficiently thin to enable single mode operation when a refractive index difference between the crystalline cladding and crystalline fiber core is ≤4×10⁻⁴ and the operational wavelength is at 1030 nm or longer.

Although embodiments have been reported herein with a crystalline fiber core and a crystalline cladding, there can be one or more layers of outer cladding atop crystalline cladding layer. The outer cladding layers can be crystalline layer or amorphous layer. Furthermore, the outer cladding layer can also be metal layer. The outer metal layer may be, for example, but is not limited to silver, aluminum, copper, gold, platinum, titanium, chromium, nickel, and combinations thereof.

D. Pre-Bending Fibers

In a further embodiment, a thin, long clad crystalline fiber may be prepared from LPE with the assistance of pre-bending the fiber for reducing the thermally induced stress, as illustrated in FIGS. 5A-5G. For example, to make a bend, first, we firmly fix one end of fiber on the holder (e.g., by high temperature adhesive). Then, we apply a pressure on the fiber core in the direction perpendicular to the fiber axis to bend the fiber. The length of the bent fiber will be at least 0.01% longer than the corresponding straight fiber. While maintaining the bending status with the applied pressure, we firmly fix the other end of fiber (e.g., by high temperature adhesive). In addition, by employing a central fixture 130, the firm holds on both ends of fiber 101 may not be need, as illustrated in FIGS. 5C and 5D. Furthermore, there can also be multiple pre-bends in the crystalline fiber as illustrated in FIGS. 5E and 5F. Moreover, there can be mesh-type bottom support to enhance the holding of the fiber, as illustrated in FIG. 5G.

E. Clad Crystalline Fibers

Clad crystalline fibers prepared by methods reported herein may have a number of properties. First, it has a crystalline fiber core and at least one layer of crystalline cladding. Second, the thickness of crystalline cladding layer is at least 1 micron and the crystalline cladding has a smooth and crack free (or minimum crack) surface. Third, the crystalline cladding should wrap the entire side surface of crystalline fiber core. Fourth, the diameter of crystalline fiber core should be less than 150 microns and the length of crystalline cladding and crystalline core fiber should be longer than 5 cm. Fifth, the refractive index of crystalline cladding layer is lower than that of crystalline fiber core.

II. Hot Isostatic Pressing (HIP)

Another embodiment pertains to a method and apparatus of producing a crystalline cladding-crystalline core fiber optical system using hot isostatic pressing (HIP). This method typically includes the following steps: (1) growing a single crystalline fiber core preform; (2) sintering a transparent polycrystalline microtube by high vacuum sintering, wherein the refractive index of polycrystalline microtube is lower than the refractive index of a single crystalline fiber core; (3) integrating the single crystalline fiber core and polycrystalline microtube together via HIP to form a unitary clad crystalline fiber; and (4) improving transmittance of the polycrystalline cladding layer via high temperature solid state conversion (SSC).

Initially, single crystalline fiber core preforms are grown using at least one growing technique, including laser heated pedestal growth (LHPG) method, micro-pulling, and edge-defined film-fed growth (EFG) method. The diameter of crystalline fiber core preform may be further reduced after growing by immersing it into under-saturated liquid phase epitaxy (LPE) flux (for example, under-saturated $Li_2MoO_4$—$MoO_3$ flux) or etching acid (for example, $H_3PO_4$ acid) before adding the crystalline cladding layer.

In some embodiments, transparent polycrystalline (for example, YAG) microtubes are produced by high vacuum sinter, similar to sintering techniques employed for aluminum oxynitride (AlON), spinel ($MgAl_2O_4$), alumina ($Al_2O_3$) transparent polycrystalline microtubes.

The fabrication of transparent polycrystalline YAG microtubes may include the following steps: (1) formulating YAG powder mixture; (2) formulating YAG paste; (3) extruding YAG paste into a microtube shape paste preform; (4) fabricating the microtube shape YAG preform; and (5) converting the microtube shape YAG preform into transparent polycrystalline YAG microtube via high vacuum sintering.

In one embodiment, a YAG powder mixture was formulated by weighting and mixing high purity grade (>99.990/%) sub-micron yttrium oxide ($Y_2O_3$) and aluminum oxide ($Al_2O_3$) powders. To obtain the YAG phase, Y:Al ratio was 3:5. A high-purity tetraethoxysilane (TEOS, 99.9999%) containing 0.14 wt % $SiO_2$, was added as a sintering aid. The powder mixture was milled in 95% ethanol for 24 hrs with high purity alumina balls and dried in a vacuum oven at 80° C. for 24 hrs.

The YAG paste was formulated by mixing the powder mixture with 50 wt % thermoplastic binder (e.g., low density polyethylene (LDPE)) to form the doped-YAG paste. The YAG paste was then extruded into a microtube shape at 150° C. and subsequently, the microtube shape YAG paste was converted into microtube shape YAG preform by pre-sintering the paste at 1200° C. for 4 hrs in air to burn out organic binder. Finally, the microtube shape YAG preform was sintered into transparent polycrystalline YAG microtube at 1650° C. for 8 hrs in a high vacuum chamber (<10⁻⁵ Pa). Transparent polycrystalline YAG microtube can be obtained within a temperature range of approximately 1600° C. to approximately 1800° C. and a time range of approximately 0.1 hr to approximately 1,000 hrs. Also, above process can also be used to fabricate other pure and/or doped crystalline materials including but not limited to pure and/or doped garnet $(Y_{1-x-y-z},Gd_x,Lu_y,Tb_z)_3(Al_{1-w},Ga_w)_5O_{12}$, where x, y, z, and w are within the range of 0 to 1, pure and/or doped yttrium orthovanadate ($YVO_4$), pure and/or doped gadolinium orthovanadate ($GdVO_4$), pure and/or doped alumina ($Al_2O_3$), pure and/or doped spinel ($MgAl_2O_4$), pure and/or doped aluminum oxynitride (AlON), pure and/or doped yttria ($Y_2O_3$), pure and/or doped zirconia ($ZrO_2$), pure and/or doped aluminum nitride (AlN), pure and/or doped yttrium iron garnet (YIG). The dopants for the core and/or cladding can be selected from the group consisting of erbium, ytterbium, neodymium, thulium, holmium, chromium, cerium, samarium, dysprosium, terbium, titanium, vanadium, magnesium, manganese, iron, cobalt, nickel, copper, bismuth, and combinations thereof.

After growing the single crystalline fiber core preform (and optionally thinned to form a single crystalline fiber core by using under-saturated flux method and/or acid etching) and fabricating the transparent polycrystalline YAG microtube, the single crystalline fiber core and polycrystalline microtube are integrated together by HIP to form a unitary clad crystalline fiber, comprising a polycrystalline cladding and a single crystalline optical fiber core.

Figure 10:
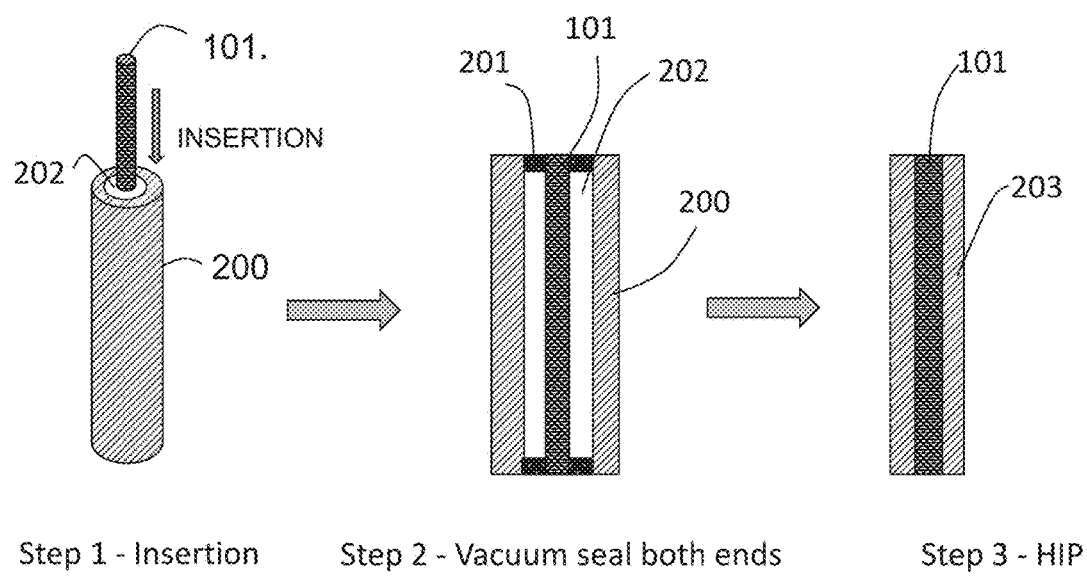
FIG. 10 shows a conceptual illustration of processes for integrating single crystal fiber core and polycrystalline microtube together by the HIP method.

Typical HIP process steps are illustrated in FIG. 10. First, a single crystalline fiber core 101 is inserted into a transparent polycrystalline YAG microtube 200. Second, the single crystalline fiber core and polycrystalline microtube are vacuum sealed at both ends 201 (for example, by melting the ends via $CO_2$ laser illumination in vacuum). Because the densely packed polycrystalline microtube has no open porosity and is impermeable to the pressuring gas, it may be used as an air-tight container for HIP processing. Finally, HIP is conducted in a non-reactive pressurized gas environment (for example, in argon gas or other gases as long as they do not react with the crystalline fiber core and polycrystalline microtube) at a temperature less than the melting temperature of the single crystalline fiber core but greater than the softening temperature of the polycrystalline microtube.

In one embodiment, the following parameters are used to integrate polycrystalline YAG microtubes with single crystalline YAG fiber cores via HIP to form unitary clad crystalline fibers: (1) argon carrier gas (or other gases as long as they do not react with the crystalline fiber core and polycrystalline microtube); (2) pressure: about 0.2 MPa to about 10,000 MPa; and temperature: about 1600° C. to about 1800° C. This temperature is less than the melting temperature of single crystalline YAG fiber core (approximately 1970° C.), but greater than the softening temperature of polycrystalline YAG microtube. Thus, the gap 202 between the single crystalline fiber core and polycrystalline microtube is collapsed during the HIP process. After the HIP process, the polycrystalline microtube 200 is converted into polycrystalline cladding 203.

Finally, to further increase the transmittance of polycrystalline cladding, a solid state conversion (SSC) process converts the polycrystalline cladding into single crystalline cladding. The single crystalline core serves as the seed to realize the solid state conversion. Since the domain boundary scattering of polycrystalline cladding is eliminated after the SSC process, scattering loss is reduced and the transmission is increased. Selection of an effective temperature is dependent upon material, for example, the optimum solid state conversion temperature is about 1700° C. to about 1800° C. for YAG crystal and about 1700° C. to about 2000° C. for sapphire crystal.

Figure 11:
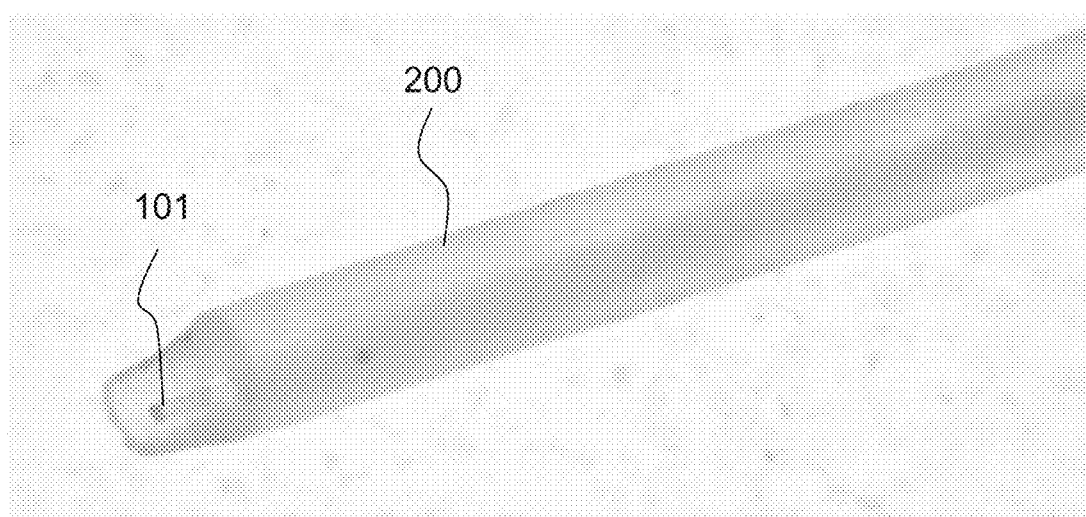
FIG. 11 shows a picture of 1% Yb doped YAG single crystalline fiber core 101 inserted into a transparent pure YAG polycrystalline microtube 200.

In one embodiment, a 1% Yb-doped YAG single crystalline fiber core was grown by the LHPG to a diameter approximately 100 μm. A pure YAG polycrystalline microtube was also produced by the high vacuum sintering method. The inner and outer diameters of the YAG polycrystalline microtube were approximately 200 μm and 600 μm, respectively. The diameter of crystalline fiber core can be within the range of approximately 10 to approximately 500 microns. The inner diameter of polycrystalline microtube can be within the range of approximately 10 to approximately 2,000 microns as long as the inner diameter of polycrystalline microtube is larger than the diameter of crystalline fiber core. There is no limitation of outer diameter of polycrystalline microtube. The refractive index of the pure YAG polycrystalline microtube was about $1 \times 10^{-4}$ less than the refractive index of the 1% Yb-doped YAG single crystalline fiber core. Since the diameter of the crystalline fiber core was less than the inner diameter of the polycrystalline microtube, the 1° % Yb-doped YAG single crystalline fiber core 101 was able to be inserted into the pure YAG polycrystalline microtube 200, as shown in FIG. 11. After that, both ends of the 1% Yb-doped YAG single crystalline fiber core and pure YAG polycrystalline microtube were sealed together by $CO_2$ laser illumination under vacuum. The sealed sample was put in a HIP furnace and treated in a non-reactive argon gas (or other non-reactive gases) environment at a pressure within a range of about 0.2 MPa to about 10,000 MPa, a temperature within a range of about 1600° C. to about 1800° C., and a time within a range of about 0.1 hr to about 10,000 hrs. After completion of the HIP process, the sample was treated in a high-vacuum furnace at a temperature within a range of about 1700° C. to about 1800° C. for YAG and about 1700° C. to about 2000° C. for sapphire and a time within a range of about 0.1 hr to about 10,000 hrs for solid state conversion.

Figure 12:
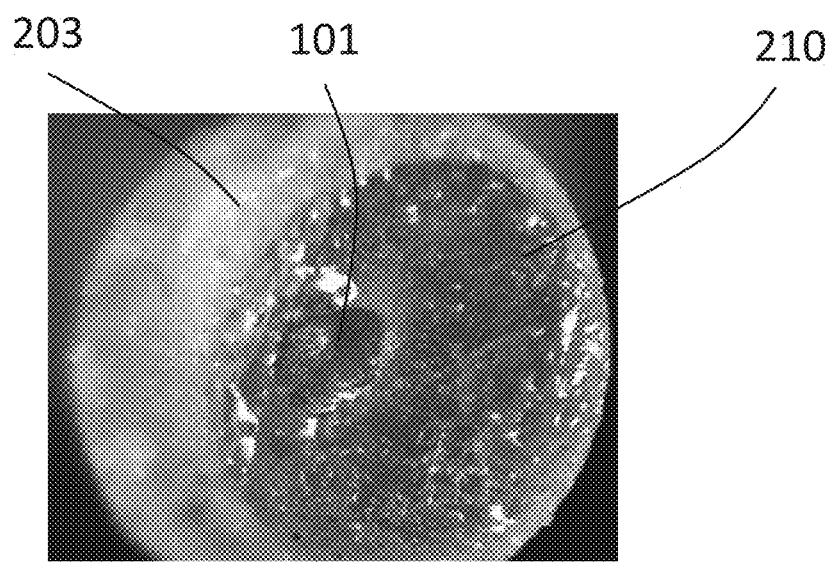
FIG. 12 shows a picture of solid state converting a portion of polycrystalline cladding 203 into a single crystalline cladding 210.

FIG. 12 illustrates the result after solid state conversion. A portion of polycrystalline cladding near the single crystalline fiber core 101 was converted into single crystalline cladding 210 while other portions of polycrystalline cladding located a distance further from the single crystalline fiber core 101 than the single crystalline cladding 210 was maintained in a polycrystalline state 203. Finally, high pressure may also be combined with the liquid phase crystal growing method to reduce the growing temperature during the liquid phase crystal growing process.

III. Applications for Crystalline-Cladding and Crystalline-Core Fiber

The crystalline cladding-crystalline core fiber optical system fabricated by methods disclosed herein have many different applications. These include, for example, but are not limited to fiber lasers, fiber amplifiers, fiber optic sensors, and all-fiber optical insulators.

Figure 13:
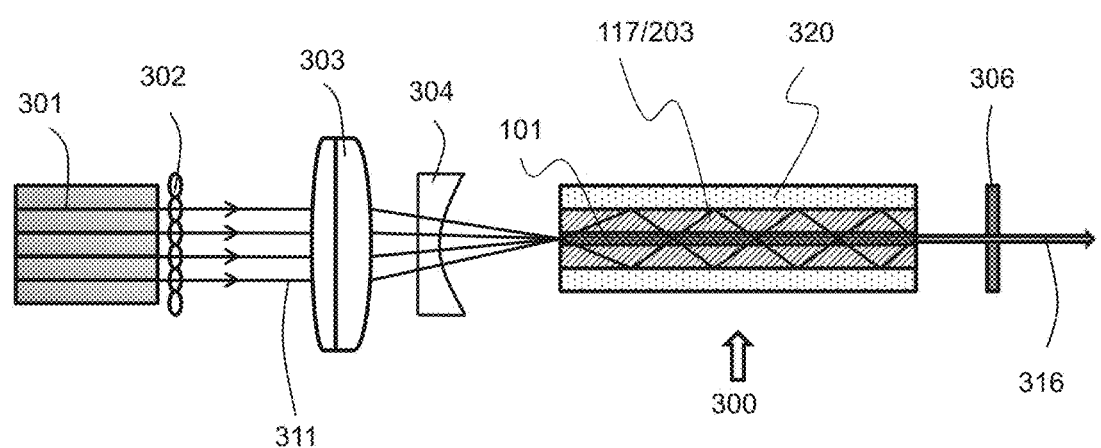
FIG. 13 shows a schematic drawing of a cladding pumped fiber laser based on the crystalline cladding and crystalline core optical fiber taught by the present invention.

FIG. 13 illustrates a cladding pumped fiber laser, in which the crystalline cladding and crystalline core optical fiber serves as a lasing medium. In this application, the crystalline cladding serves as an inner cladding. Optionally, a thin outer cladding (for example, less than 10 μm) may be included whose refractive index is lower than the refractive index of the inner cladding. Because the outer cladding is very thin, thermal conductivity does not create much heat dissipation issues and can be made from either crystalline or amorphous materials.

The cladding pumped fiber laser includes a pump laser 301 that emits a pump laser beam 311 at pump wavelength $\lambda_{pump}$, a pump laser beam collimator 302, a focusing lens 303 that focuses the pump laser beam 311 into inner crystalline cladding 117/203 and crystalline fiber core 101, a dichroic mirror 304 that transmits pumping wavelength $\lambda_{pump}$ and reflects lasing wavelength $\lambda_{lasing}$, a crystalline cladding and crystalline core optical fiber 300 that consists of a crystalline fiber core 101, a crystalline inner cladding 117/203, and a thin outer cladding 320, and an output coupler 306 that partially reflects the lasing wavelength $\lambda_{lasing}$. The dichroic mirror 304 and output coupler 306 form a laser resonant cavity. An output laser beam 316 emits out from the output coupler 306. Since heat is easily transferred out by the high thermal conductivity crystalline core and crystalline inner cladding, a high power/energy fiber laser can be realized by using the crystalline cladding and crystalline core fiber disclosed herein. To reduce reflection loss, anti-reflection coating for the pumping wavelength may optionally be added on end surfaces of both the crystalline cladding and crystalline core optical fiber.

Figure 14:
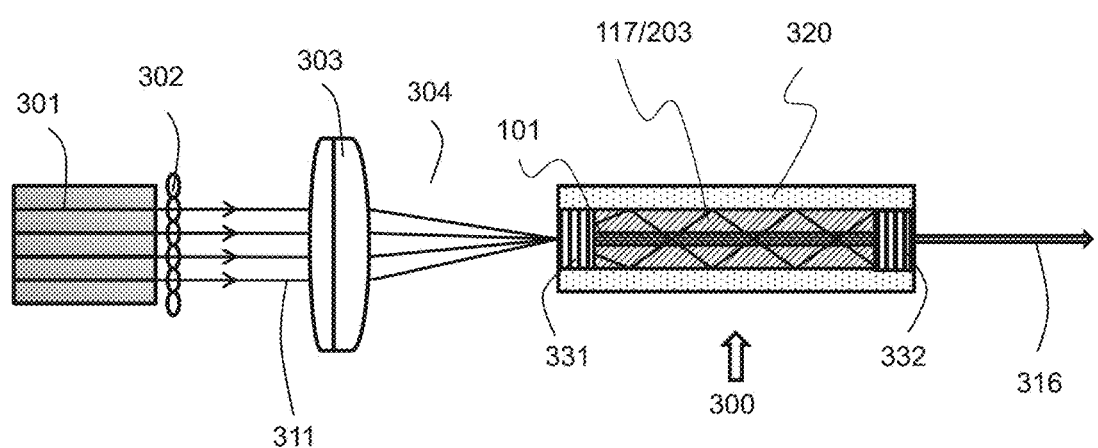
FIG. 14 shows a schematic drawing of a cladding pumped fiber laser including the in-fiber Bragg gratings in crystalline cladding and crystalline core optical fiber.

A modified cladding pumped fiber laser is formed by replacing the dichroic mirror 304 and/or output coupler 306 with in-fiber Bragg gratings. A total-reflection Bragg grating 331 reflects the lasing wavelength $\lambda_{lasing}$ and a partial-reflection Bragg grating 332 partially reflects the lasing wavelength $\lambda_{lasing}$, as illustrated in FIG. 14. Such in-fiber Bragg gratings can be inscribed in the crystalline fiber core by femtosecond laser illumination.

Figure 15:
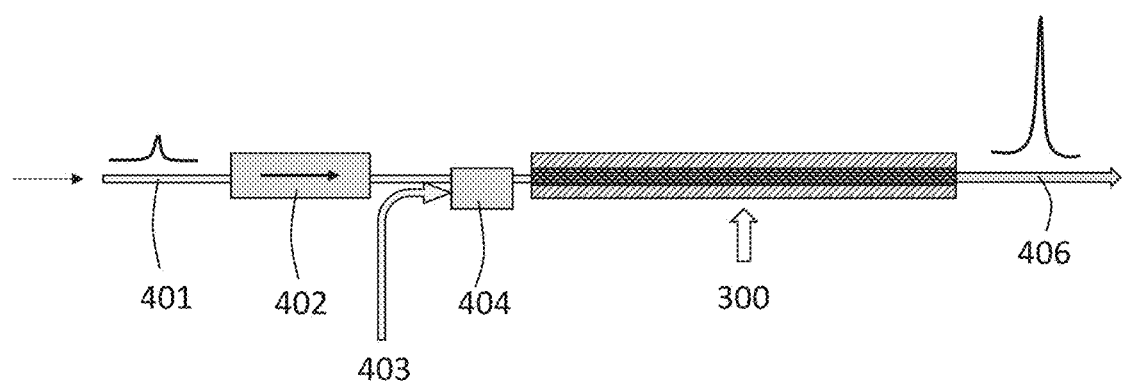
FIG. 15 shows a schematic drawing of fiber amplifier based on crystalline cladding and crystalline core optical fiber.

FIG. 15 illustrates a high efficiency fiber amplifier based on the crystalline cladding-crystalline core fiber optical system disclosed herein. An incoming signal beam 401 first passes through an isolator 402 and then both the signal beam 401 and pumping beam 403 are coupled into the crystalline cladding and crystalline fiber core 300 via a dichroic coupler

404. The crystalline fiber core is doped and absorbs the pumping wavelength light, thereby emitting a signal wavelength light. Thus, an amplified signal beam 406 can be obtained.

Figure 16:
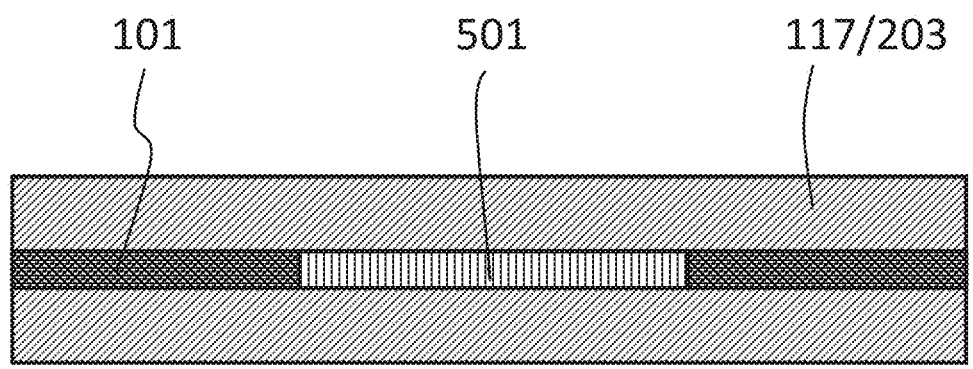
FIG. 16 shows a schematic drawing of a high performance fiber optic sensor based on in-fiber Bragg gratings inscribed in the crystalline cladding and crystalline core optical fiber.

FIG. 16 illustrates a high selectivity and sensitivity harsh environment fiber optic sensor using the crystalline cladding-crystalline core fiber optical system disclosed herein. A harsh environment sensor should work at an ambient temperature over 1000° C. and robust against chemical attacks at this elevated temperature. The high selectivity means that a sensor can be designed to sense a particular measurand (e.g., temperature or pressure) and a high sensitivity means that, in terms of temperature sensor it can have a sensitivity better than 1% of sensing range. Since crystalline cladding and crystalline core fibers (for example, sapphire and YAG) have high melting temperatures (for example, at least 1800° C.) and are highly robust against chemical attacks, harsh environment high temperature fiber optic sensors can be developed. Furthermore, since fewer even single mode operation can be achieved by employing the crystalline cladding-crystalline-core fiber optical system disclosed herein, a high performance fiber optic sensor can be fabricated from a well-controlled light beam profile. Sensitivity and selectivity are further improved by creating micro/nano structures on fiber. For example, by inscribing in-fiber Bragg grating 501 in the crystalline fiber core 101 and/or crystalline fiber cladding 117/203, a high selectivity and sensitivity harsh environment fiber optic sensor can be realized.

For the disclosed devices according to fabrication methods disclosed herein, Bragg resonant wavelength, $\lambda_B$, can be written as:

$$m \cdot \lambda_B = 2 n_{eff} \cdot \Lambda, \qquad (2)$$

wherein m is an integer, $n_{eff}$ is the effective refractive index of the fiber core, and $\Lambda$ denotes the period of Bragg grating. Changes in temperature and/or pressure changes the effective refractive index $n_{eff}$ and/or grating period $\Lambda$, which consequently changes the Bragg wavelength $\lambda_B$. Thus, by measuring the shifts of Bragg wavelength (for example, by a compact spectrometer), the changes in temperature and pressure can also be determined. In addition to Bragg grating, the long period grating (LPG) that couples the core and cladding mode can also be inscribed in the crystalline core and cladding fiber to further enhance the sensitivity of fiber optic sensors.

Figure 17:
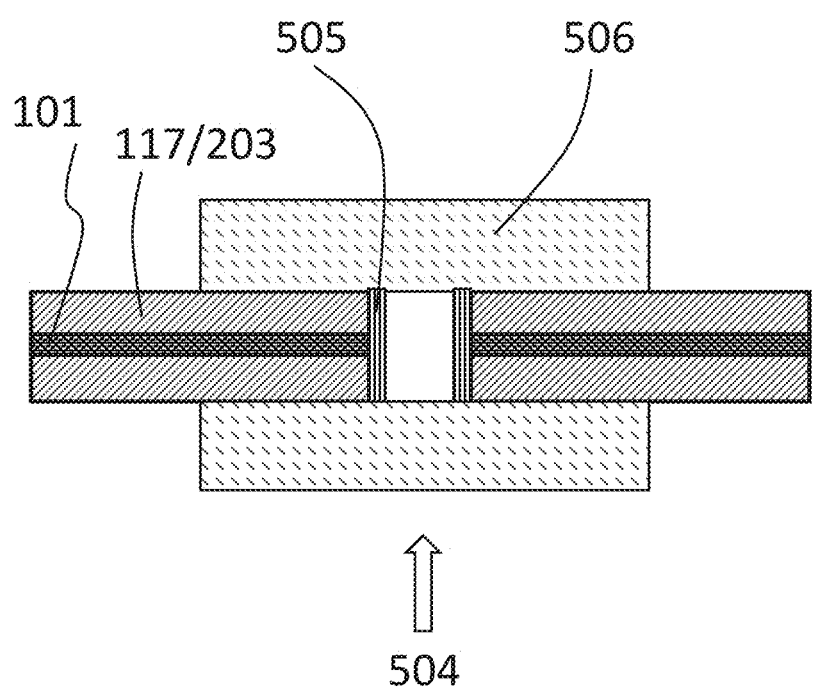
FIG. 17 shows a schematic drawing of a high performance fiber optic sensor based on a fiber Fabry-Perot cavity built with crystalline cladding and crystalline core optical fiber.

A modified fiber optic sensor may be fabricated according to FIG. 17 wherein the sensitivity and selectivity of the modified fiber sensor is enhanced by creating a Fabry-Perot resonant cavity 504 composed of crystalline cladding and crystalline fiber core, reflection coatings 505 on end surfaces of the crystalline fiber core and/or crystalline cladding, and holding sleeve 506. Sensitivity of temperature sensor is within 1% of sensing range or better. The sensitivity of pressure sensor will be better than $10^{-7}$/kPa. In terms of selectivity, the cross-talk from non-measurands is less than 50%. The shift of resonant wavelength of the Fabry-Perot resonant cavity 504 allows for determination of things such as temperature and pressure.

Figure 18:
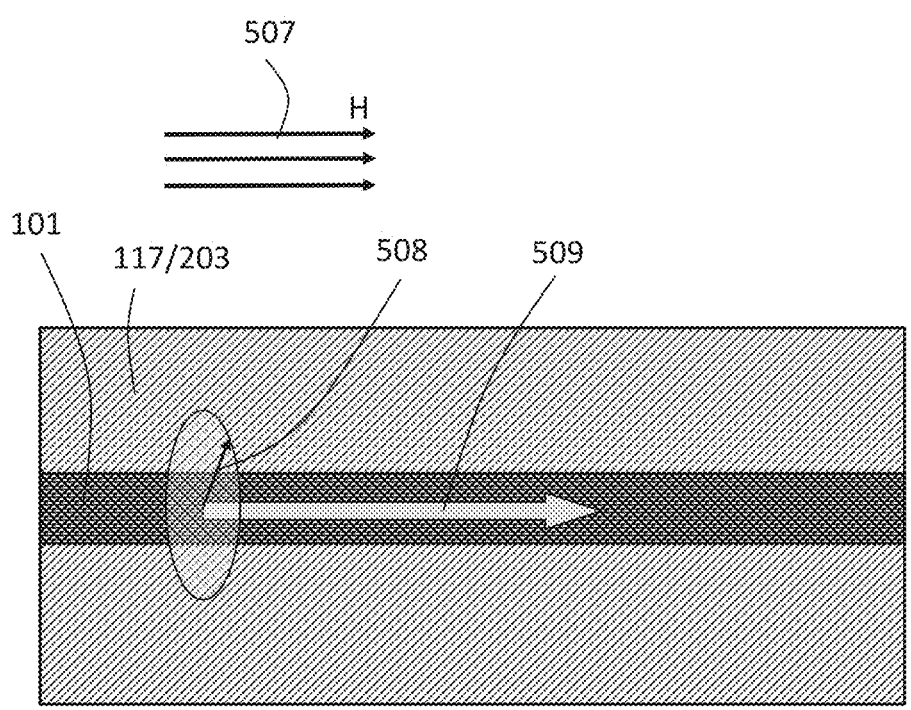
FIG. 18 shows a schematic drawing of a high sensitivity fiber optic magnetic field sensor based on magneto-optic crystalline cladding and crystalline core optical fiber.

A magnetic field sensor may also be fabricated according to FIG. 18 using a Bi-substituted yttrium iron garnet (YIG) crystalline fiber having a large Verdet magneto-optic constant (better than 1 deg/μm at a saturation magnetic field and at an operational wavelength of 633 nm) to realize a high sensitivity and high selectivity magnetic field sensor. The magnetic field sensitivity is better than 100 deg/Oe at an operational wavelength of 633 nm. Because fiber length is long (e.g., ≥10 cm), a small change in magnetic field 507 (e.g., 1 Oe) results in a large change in polarization direction 508 (e.g., >100 deg at an operational wavelength of 633 nm) of propagated light beam 509 within the fiber. Fiber optic sensors of the type disclosed herein, for example in FIG. 18, have applications in, for example, automatic navigation systems and smart electric grids.

Figure 19:
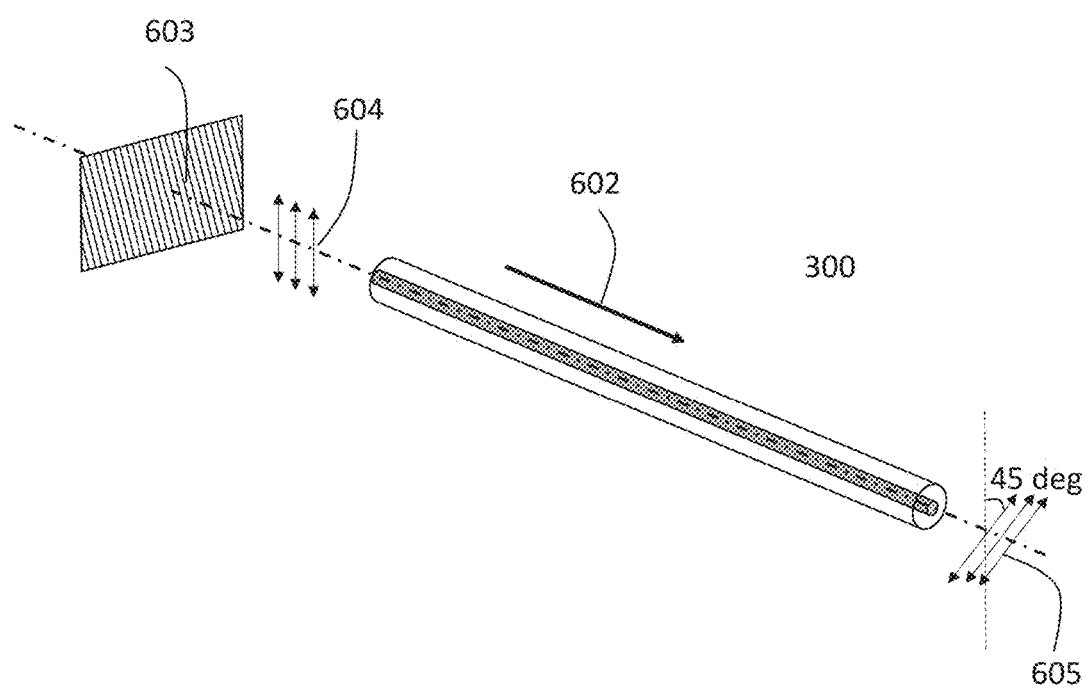
FIG. 19 shows a schematic drawing of an all-fiber optical isolator based on magneto-optic crystalline cladding and crystalline core optical fiber.

A compact (with a transversal dimension less than 4 mm×4 mm) all-fiber optic isolator may be fabricated according to FIG. 19 and comprises a magneto-optic crystalline cladding and crystalline core optical fiber 300, a magnetic field 602, and a polarizer 603, wherein the polarizer may be selected from the group consisting of an absorption-based polarizer; a birefringent-based polarizer; and a metallic nanogrid-based polarizer. The length and magnetic field are selected such that polarization of incoming light 604 is rotated by an angle 605 (for example, 45°) after passing through fiber 300. Since the back propagated light will be rotated by another 45°, it will be blocked by polarizer 603 such that an all-fiber optical isolator is realized. Because the crystalline cladding and crystalline core optical fiber is made from magneto-optic materials such as Bi- and/or Ce-substituted crystalline YIG, the all-fiber optic isolator has a large Verdet magneto-optic constant (better than 1 deg/μm at a saturation magnetic field and at an operational wavelength of 633 nm).

Alternatively, the crystalline cladding and crystalline core optical fiber may also be made from electro-optic materials such as potassium tantalate niobate (KTN), lithium niobate ($LiNbO_3$), and lithium tantalate ($LiTaO_3$) or piezoelectric materials such as barium titanate ($BaTiO_3$), lanthanum doped lead zirconate-titanate (PLZT), and lead magnesium niobate-lead titanate (PMN-PT), to form devices for sensing electric field, stress, and pressure.

Figure 20:
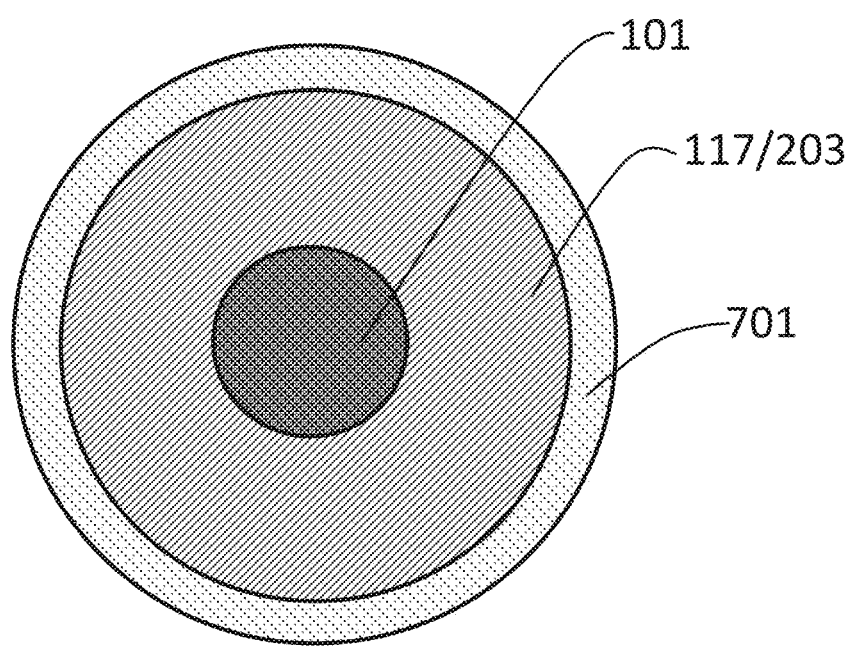
FIG. 20 shows an illustration of crystalline core and crystalline cladding optical fiber containing multiple cladding layers, including a crystalline core 101, an inner crystalline cladding 117/203 that has a refractive index lower than that of crystalline core, and an outer (crystalline or amorphous) cladding 701 that has a refractive index lower than that of crystalline inner cladding.
Figure 21:
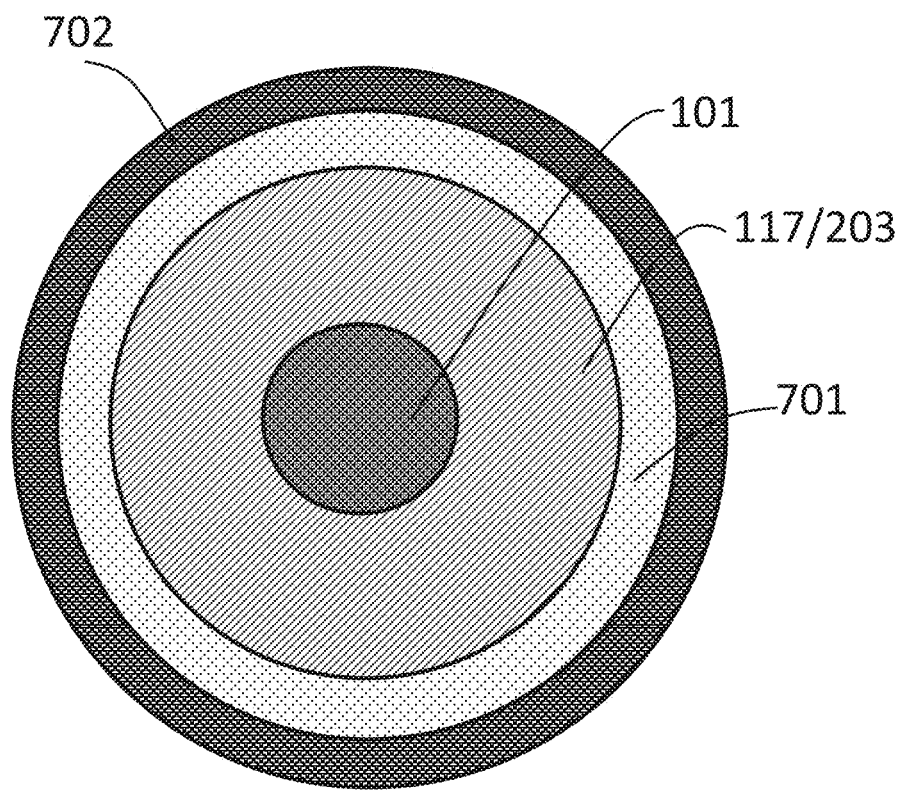
FIG. 21 shows an illustration of a metal overlay layer 702 on top of outer cladding layer 701.

In one embodiment, the devices disclosed herein by way of FIGS. 13-19 may comprise an outer cladding layer and an inner crystalline cladding layer, wherein the refractive index of the outer cladding layer is lower than the refractive index of the inner crystalline cladding layer. The outer cladding layer can be crystalline cladding formed by either LPE or HIP fabrication methods or amorphous cladding formed by dipping in a molten glass or by physical vapor deposition (including but not limited to vacuum evaporation, sputtering, pulsed laser deposition) or by chemical vapor deposition (including but not limited to chemical vapor deposition, metalorganic chemical vapor deposition, molecular beam epitaxy, atomic layer deposition) or by chemical and electrochemical methods (including but not limited to anodizing, plating), or by spraying or by roll-to-roll coating processing (including but not limited to hot melt coating, printing, lithography). FIG. 20 illustrates a crystalline cladding-crystalline core fiber optical system having a crystalline fiber core 101, an inner crystalline cladding layer 117/203 having a refractive index lower than the refractive index of the crystalline fiber core 101, and an outer crystalline and/or amorphous cladding layer 701 having a refractive index lower than the refractive index of the inner crystalline cladding layer 117/203. FIG. 21 illustrates an optional outer metal layer 702 overlaying the outer cladding layer 701, wherein the outer metal layer 702 is selected from the group consisting of including but not limited to silver, aluminum, copper, gold, platinum, titanium, chromium, nickel and combinations thereof.

Figure 22:
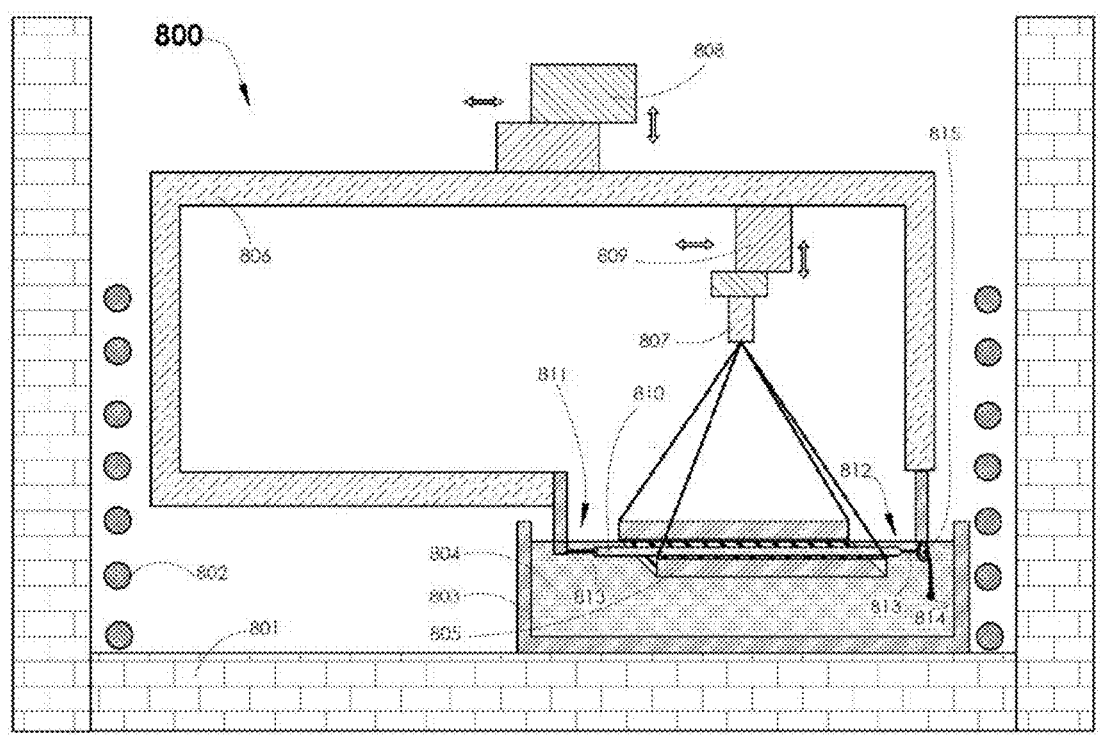
FIG. 22 illustrates an apparatus 800 for growing crystalline cladding and crystalline core fiber, in which the fiber and the holding basket are immersed in the molten growing flux.

FIG. 22 illustrates an apparatus 800 for growing crystalline cladding and crystalline core fiber, which is composed of (1) a growing furnace including thermal insulation bricks 801, heating elements 802, and the corresponding power supply and controller, (2) a crucible 803, (3) flux 804 for crystal growth, (4) a holding basket 805, (5) a fiber holder 806, (6) a basket holder 807, (7) a fiber holder moving stage 808, (8) a basket holder moving stage 809, (9) the crystalline fiber 810, (10) a firm fixed fiber end 811, including a holding wire 813 connecting fiber and fiber holder, (11) a soft fixed fiber end 812, including a holding wire 813, a tiny weight 814, and a ring shape pulley 815. The soft fixed fiber end 812 is holding by the weight 814.

The soft end holding is used to minimize thermally-induced stress during temperature ramp-up and/or cooling down during the growing process, which in turn reduces the risk of damaging the fiber 810. The bottom of holding basket 805 also includes one-dimensional (1D) or two-dimensional (2D) meshes, which allows the molten flux to pass through while providing the vertical support of fiber. Furthermore, there is a relative movement between the fiber 810 and the holding basket 805 in at least fiber axial direction during the growing process while they maintain in contact in the vertical direction, which ensures a uniform fiber core and a uniform fiber cladding. Furthermore, in addition to a relative movement, both the fiber seed 810 and the holding basket 805 can move within the molten flux to further enhance uniform etching and growth.

Figure 23:
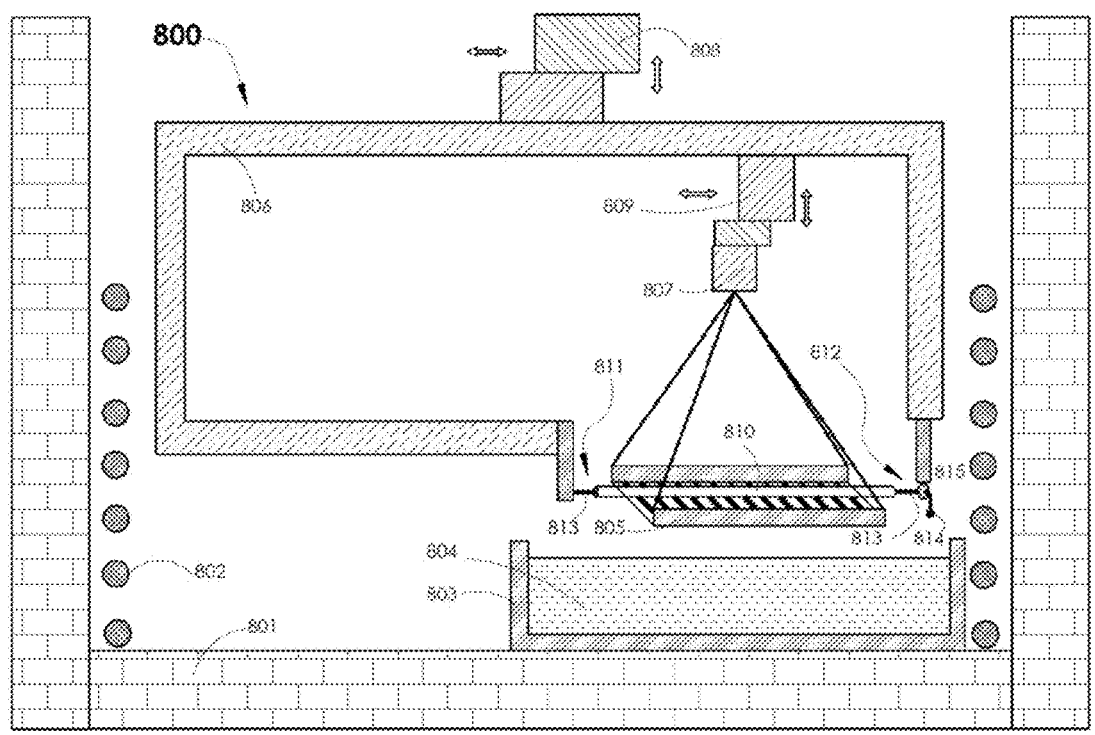
FIG. 23 illustrates an apparatus 800 for growing crystalline cladding and crystalline core fiber, in which the fiber and the holding basket are moved out of the molten growing flux.

After the growth, the grown crystalline cladding and crystalline core fiber 810 and the holding basket 805 are moved out of the molten flux simultaneously, as illustrated in FIG. 23, which minimizes the risk of damaging the fiber by the drag force of viscous flux and the surface tension force of the flux at the moment of fiber being pulled out of the surface.

Figure 24:
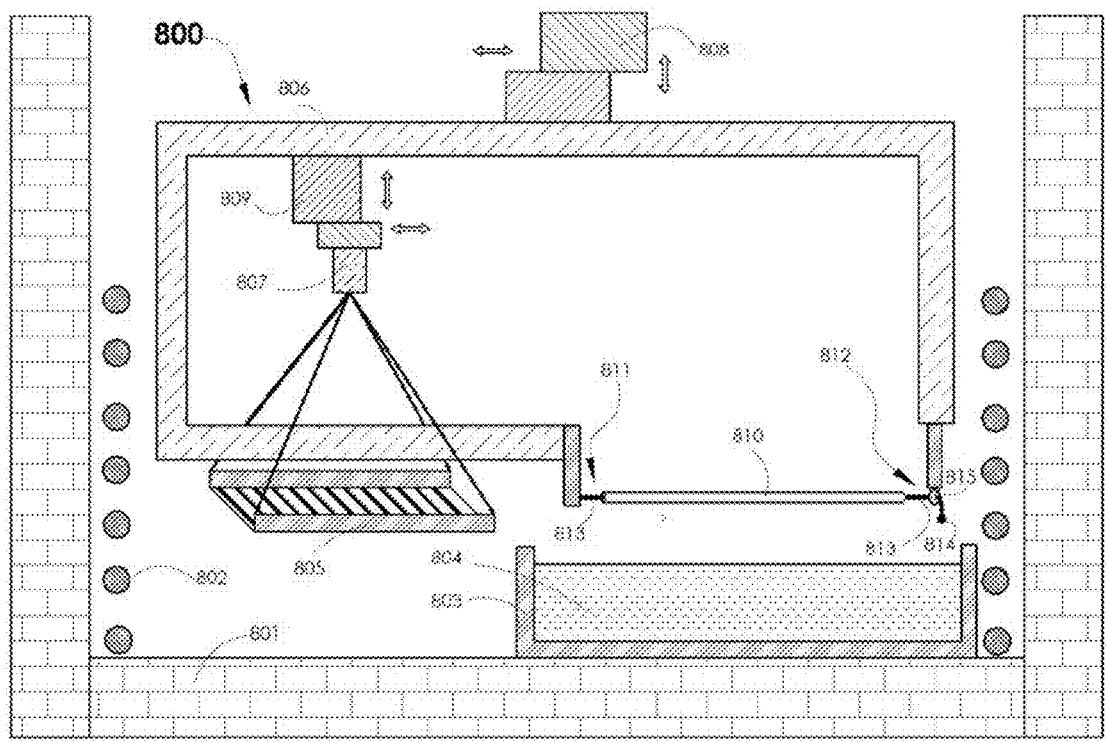
FIG. 24 illustrates an apparatus 800 for growing crystalline cladding and crystalline core fiber, in which the fiber and the holding basket are separated.

Furthermore, the fiber 810 and the holding basket 805 are separately by creating the relative translation between the fiber and/or basket along the fiber axial direction while the flux is still at the molten liquid state, as illustrated in FIG. 24. This avoids the fiber 801 and the basket 805 are bonded together by the solidified flux. Since the fiber 801 and the basket 805 can have different thermal expansion coefficients, the bonded fiber can be damaged by the thermal stress if they are not separated. This separation method minimizes/reduces the risk of damaging the fiber by the solidification of flux induced thermal stress.

IV. Advantages Over Other Methods

As reported below, embodiments as reported herein are typically superior to past attempts at making crystalline cladding and crystalline core optical fibers A. Glass Cladding and Crystalline Core Fibers Glass cladding and crystalline core optical fibers are known. These are fundamentally different from the crystalline cladding and crystalline core optical fibers, as reported herein.

At the earlier stage of glass cladding/crystalline core optical fiber, glass cladding was formed by directly pulling the crystalline fiber cores from melted glass (e.g., Byer et al, U.S. Pat. No. 5,077,087). More recently, parties reported a method of making glass cladding and crystalline core fiber by heating a composite preform comprising a crystalline core and a glass capillary tube (e.g., by a $CO_2$ laser illumination, Hsu, et al, US patent application 2014/0079363).

Unfortunately, although it is a relatively ease approach to clad the crystalline fiber core with a glass cladding, above approaches suffer from following fundamental limitations. First, the thermal conductivity of glass cladding is only around 1-2 W/m·K, which is much lower than that of crystalline fiber core (e.g., ~10 W/m·K for YAG fiber core). Thus, one of the major advantages of crystalline fiber—high thermal conductivity is largely compromised. Second, even with careful selection, the thermal expansion coefficient of glass cladding cannot perfectly match the thermal expansion coefficient of crystalline core, which can introduce mechanical stresses and cause the damage to the crystalline fiber core and/or glass cladding during the cooling, in particular, for the thin and long fiber cores. Finally, the relatively low softening/melting temperature of glass cladding (e.g., <1000° C.) makes the glass cladding/crystalline core fiber not suitable for high temperature (>1000° C.) fiber optic sensor application.

B. Modified Laser Heated Pedestal Growth (m-LHPG)

To form gradient index crystalline fibers, another previously attempted approach was to take advantage the movement of the rare earth ions within the melted crystalline preform by a modified LHPT method (e.g., Rusanov et al, U.S. Pat. No. 5,579,427), in which a thermal gradient was created with temperature peaking at the center of the molten zone. Although this approach may work for certain rare earth ion dopants (e.g., Nd), it does not work for other dopants (e.g., Er, Yb, Ho). For many dopants such as Er, Yb, Ho, the high mobility of liquid state uniformizes the dopant concentrations, which make it hard form a graded index and/or crystalline cladding and crystalline core optical fiber.

C. Other Coating Methods

There have been efforts to create cladding on crystalline core fiber by conventional coating methods such as sol-gel, evaporation, sputtering, and pulse laser deposition. However, it is very difficult to achieve low loss single crystalline cladding by these conventional coating methods. Furthermore, the coated films could have crack problem due to the mismatched thermal expansion coefficient and/or densification induced stress during the thermal annealing process. The problem could become severe when the coated films were thick.

D. Crystalline Films Attempted to be Grown by LPE

There have been failed efforts to grow crystalline films on thin and long crystalline fiber core by liquid phase epitaxy (LPE) and realize single or fewer mode operations. These previous efforts are entirely different from the LPE effort described in the present invention for multiple reasons. For example, none of the other LPE efforts teach the method of decreasing or precisely controlling the number of modes propagated in the crystalline cladding and crystalline core by (1) firstly reducing the crystalline fiber core diameter via an under-saturated LPE flux and then (2) growing the crystalline cladding layer on the thinned crystalline fiber core via a super-saturated LPE flux and the refractive index of grown crystalline cladding layer is different from the crystalline fiber core (e.g., lower than the refractive index of crystalline fiber core). Past attempts also failed to teach how to properly hold crystalline fiber without thermally induced stress during the LPE growing process. Their fibers, if prepared at all, would have been damaged by the thermally induced stress. Contrast that with methods reported herein, which retain the fiber without the thermally induced stress or reduced thermally induced stress such as by using pre-bent and/or one-end firmly holding method.

Older efforts also failed to teach how to use a mesh type bottom support to enhance the holding of the thin, long, fragile, and flexible crystalline fiber, as illustrated in FIG. 5G. It should be noticed that there is a relative movement between the crystalline fiber and the mesh type (1D or 2D) bottom support during the LPE growing process, which ensures a uniform cladding growth.

V. Monitoring Methods

Figure 25:
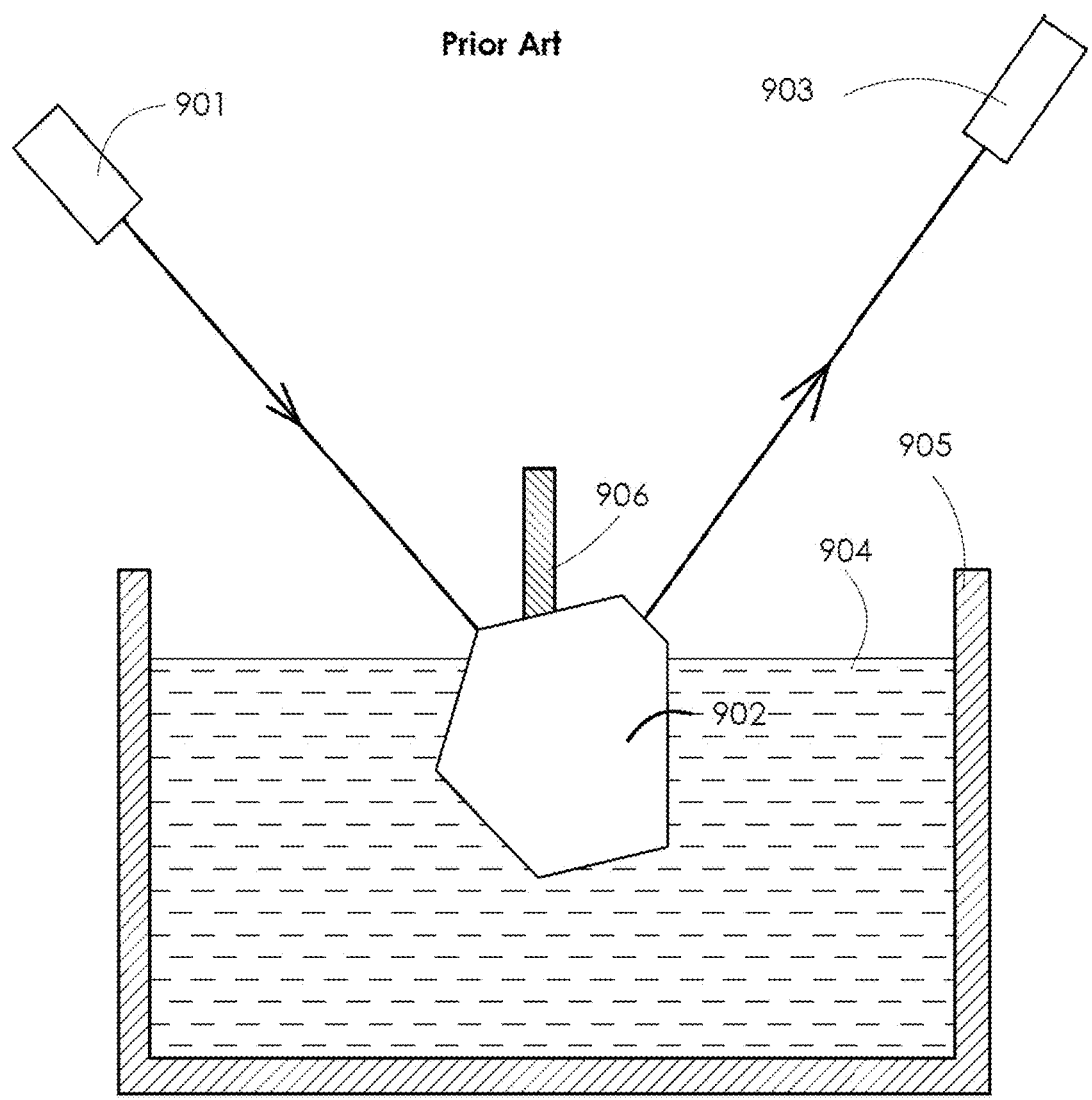
FIG. 25 illustrates a prior art method of monitoring the crystalline fiber growing process based on reflection image.

FIG. 25 illustrates a prior art method of monitoring the crystal growing process based on reflection image, which is composed of an illumination light source 901, the crystal being grown 902, the image detector 903, the growing flux 904, the growing crucible 905, the holder for the crystal seed 906. As described in the section of induction, this method is only suitable for the cases when there is a large contrast difference between the refractive index of the crystalline fiber being grown and the surrounding growing flux.

Figure 26:
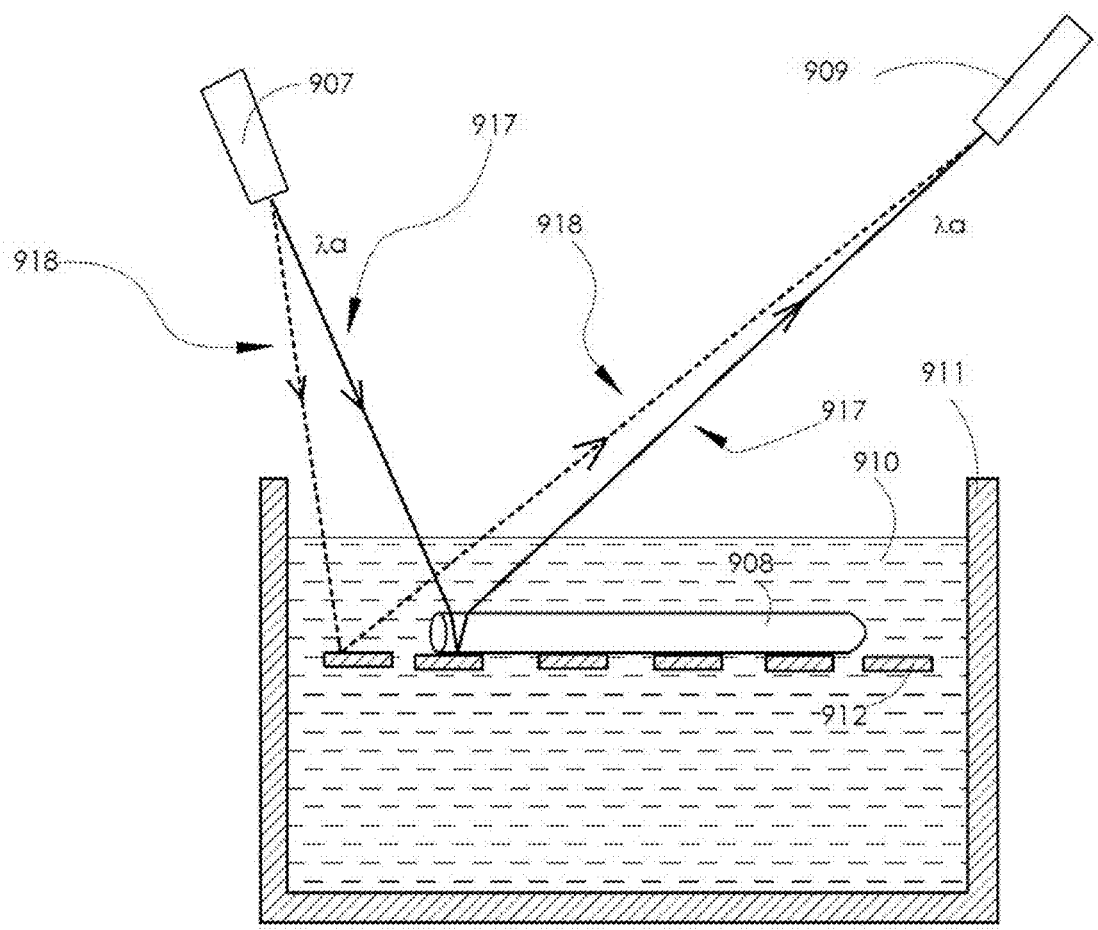
FIG. 26 illustrates a method of monitoring the crystalline fiber growing process based on absorption image taught in this invention.

FIG. 26 illustrate a method of monitoring the crystalline fiber growing based on resonant absorption image taught in this invention, which is composed of an illuminating light source 907 that emits the wavelength, $\lambda_a$, corresponding to one or more absorption peaks of the being grown crystalline fiber 908, the image detector 909 that detects the illuminating wavelength/wavelengths, $\lambda_a$, the growing flux 910, the growing crucible 911, the mesh type bottom holder 912. For example, in terms of thulium (Tm) doped/co-doped YAG, the absorption peaks at UV-VIS-IR spectral range are 262 nm, 357 nm, 460 nm, 681 nm, 785 nm, 1172 nm, and 1622 nm, respectively. To minimize the cross-talk from the blackbody radiation at high temperature and potential UV absorption of some fluxes (e.g., the flux containing $MoO_3$), 460 nm will be one of the preferred wavelengths to be used for illumination. The illuminated light can pass through the crystalline fiber (at least partially absorbed by the fiber because the illuminating wavelength corresponds to at least one absorption peaks of the being grown crystalline fiber) and then be reflected by the bottom of crucible and/or mesh type supporter. The reflected light beam passes through the crystalline fiber again and then is detected by 909 (i.e., light ray 917). Or the illuminated light directly hits the bottom or side walls of the crucible or bottom mesh support and then the reflected light beam is detected by the detector 909 (i.e., light ray 918). Since this light beam does not pass through the crystalline fiber and it does not have the absorption from the crystalline fiber, a higher light intensity reaches the detector. Thus, a high contrast ratio absorption image of the crystalline fiber can be obtained, which can be used to monitor the geometry the crystalline fiber being grown.

Figure 27:
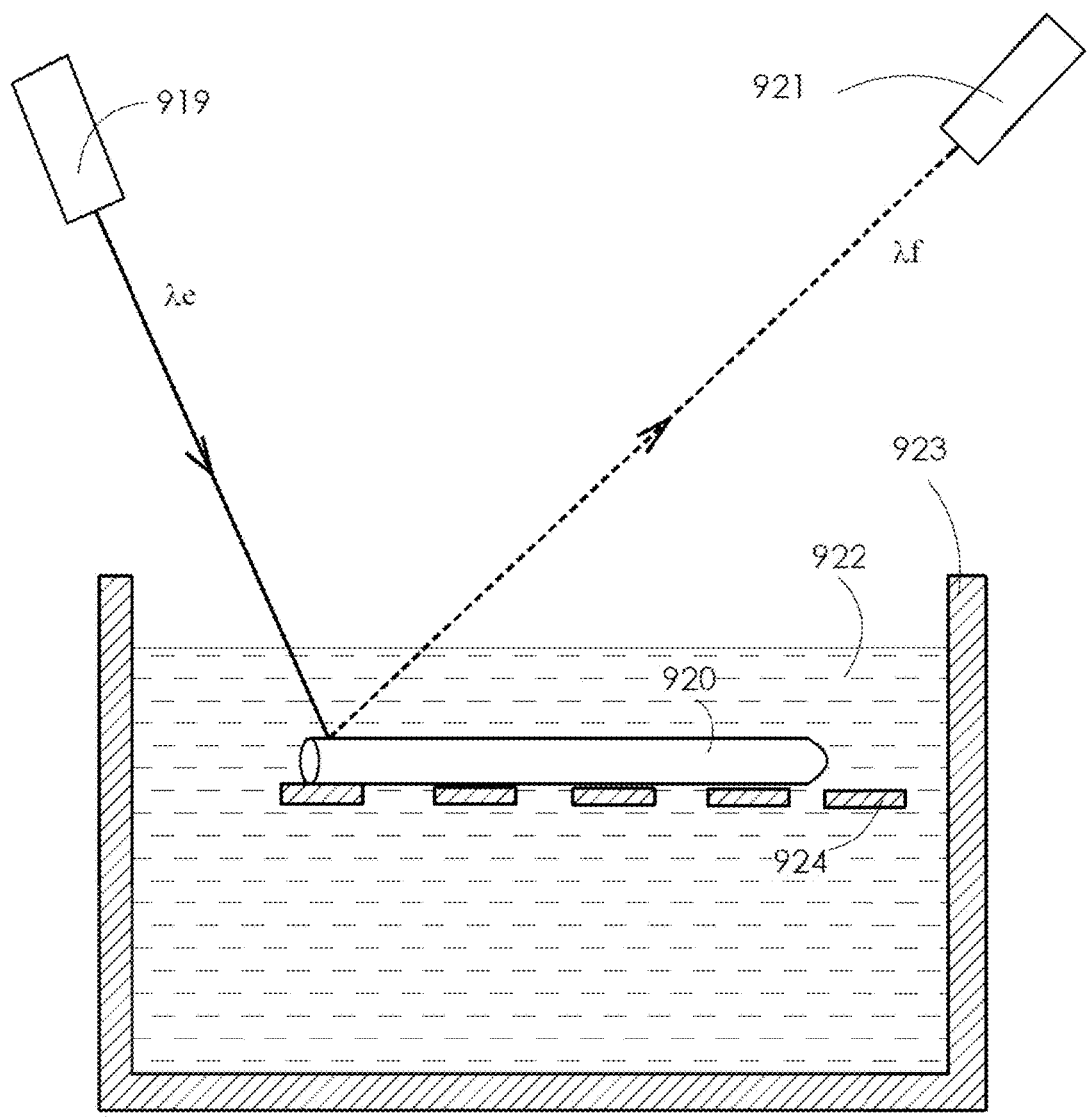
FIG. 27 illustrates a method of monitoring the crystalline fiber growing process based on fluorescent image taught in this invention.

FIG. 27 illustrates a method of monitoring the crystalline fiber growing process based on fluorescent image, which is composed of an illuminating light source 919 that emits the wavelength corresponding to one or more exciting wavelengths, $\lambda_e$ of being grown crystalline fiber 920, the imaging detector 921 that only detects the excited fluorescent wavelength/wavelengths, $\lambda_f$, the growing flux 922, the growing crucible 923, the mesh type bottom holder 924. For example, in terms of thulium (Tm) doped/co-doped YAG, The excitation wavelength can be 357 nm and the detected fluorescent wavelength can be 456 nm. Since the area with crystalline fiber emits fluorescent light and the ambient flux does not emit fluorescent light, a clear fluorescent image of crystalline fiber can be obtained, which can be used to determine the size (e.g., the diameter) of the fiber being grown in real time.

The invention having been described in detail, those skilled in the art will appreciate that, given the disclosure herein, modification may be made to the invention without departing from the spirit of the invention concept. It is not intended that the scope of the invention be limited to the specific and preferred embodiments illustrated and described. All documents referenced herein are hereby incorporated by reference, with the understanding that where there is any discrepancy between this specification and the incorporated document, this specification controls.

We claim:

1. A method for preparing a crystalline clad and crystalline core optical fiber, comprising:

securing a crystalline fiber core having a refractive index and a first end and a second end in a holder with no or minimized thermally induced stress, wherein the first end of the crystalline fiber core is secured in the holder and wherein the second end is free to move in at least an axial direction of the fiber within the holder;

immersing the crystalline fiber core into at least one molten liquid phase epitaxy (LPE) solution comprising at least one flux and at least one cladding until a crystalline cladding layer has formed thereon, said crystalline cladding layer having a lower refractive index than the crystalline fiber core refractive index;

further comprising adding the molten LPE solution through a 1-dimensional or 2-dimensional mesh type bottom support, wherein the molten flux passes through the mesh type bottom support and there is a relative movement between the fiber core preform and mesh bottom support along at least the axial direction of the fiber during an LPE growing process, resulting in a uniform cladding growth, wherein the crystalline fiber core and mesh type bottom support is separated while the molten flux is still at a molten liquid state by creating a relative translation along an axial direction of the crystalline fiber core, after the crystalline fiber core and mesh bottom support are pulled out of the crucible.

2. The method of claim 1, wherein both the mesh bottom support and the fiber can move within the flux in addition to the relative movement between two.

3. The method of claim 1, wherein the flux is selected from the group consisting of $Li_2MoO_4$—$MoO_3$, $Y_2O_3$, $Al_2O_3$, $Yb_2O_3$, PbO—$B_2O_3$, BaO—$B_2O_3$—$BaF_2$, PbO—$PbF_2$—$B_2O_3$, PbO—$V_2O_5$, PbO—$PbF_2$, KF—MoO3, KF—$BaTiO_3$, $K_2CO_3$, $PbF_2$—$B_2O_3$, and $MoO_3$—$K_2MoO_4$—$Y_2O_3$.

4. The method of claim 1, wherein the cladding material is selected from the group consisting of pure and/or doped garnet $(Y_{1-x-y-z}, Gd_x, Lu_y, Tb_z)_3(Al_{1-w}, Ga_w)_5O_{12}$, where x, y, z, and w are within the range of 0 to 1, pure and/or doped yttrium lithium fluoride (YLF), pure and/or doped yttrium orthovanadate ($YVO_4$), pure and/or doped gadolinium orthovanadate ($GdVO_4$), pure and/or doped colquiriite (LiSaF), pure and/or doped alumina ($Al_2O_3$), pure and/or doped spinel ($MgAl_2O_4$), pure and/or doped aluminum oxynitride (AlON), pure and/or doped yttria ($Y_2O_3$), pure and/or doped zirconia ($ZrO_2$), pure and/or doped aluminum nitride (AlN), pure and/or doped yttrium iron garnet (YIG), pure and/or doped potassium tantalate niobate (KTN), pure and/or doped lithium niobate ($LiNbO_3$), pure and/or doped tantalate niobate ($LiTaO_3$), pure and/or doped lanthanum lead zirconate-titanate (PLZT), pure and/or doped lead magnesium niobate-lead titanate (PMN-PT), gallium arsenide (GaAs), gallium aluminum arsenide (GaAlAs), gallium nitride (GaN) and combinations thereof.

5. The method of claim 1, wherein the crystalline fiber core is selected from the group consisting of doped garnet $(Y_{1-x-y-z}, Gd_x, Lu_y, Tb_z)_3(Al_{1-w}, Ga_w)_5O_{12}$, where x, y, z, and w are within the range of 0 to 1, pure and/or doped yttrium lithium fluoride (YLF), pure and/or doped yttrium orthovanadate ($YVO_4$), pure and/or doped gadolinium orthovanadate ($GdVO_4$), pure and/or doped colquiriite (LiSaF), pure and/or doped alumina ($Al_2O_3$), pure and/or doped spinel ($MgAl_2O_4$), pure and/or doped aluminum oxynitride (AlON), pure and/or doped yttria ($Y_2O_3$), pure and/or doped zirconia ($ZrO_2$), pure and/or doped aluminum nitride (AlN), pure and/or doped yttrium iron garnet (YIG), pure and/or doped potassium tantalate niobate (KTN), pure and/or doped lithium niobate ($LiNbO_3$), pure and/or doped tantalate niobate (LiTaO₃), pure and/or doped lanthanum lead zirconate-titanate (PLZT), pure and/or doped lead magnesium niobate-lead titanate (PMN-PT), gallium arsenide (GaAs), gallium aluminum arsenide (GaAlAs), gallium nitride (GaN) and combinations thereof.

\* \* \* \* \*